US011857150B2

(12) United States Patent
Takenouchi et al.

(10) Patent No.: US 11,857,150 B2
(45) Date of Patent: Jan. 2, 2024

(54) SIGNAL PROCESSING APPARATUS

(71) Applicant: Sony Olympus Medical Solutions Inc., Tokyo (JP)

(72) Inventors: Yusuke Takenouchi, Saitama (JP); Aki Mizukami, Kanagawa (JP); Masashige Kimura, Tokyo (JP); Satoshi Taira, Tokyo (JP); Keisuke Takahashi, Tokyo (JP)

(73) Assignee: Sony Olympus Medical Solutions Inc., Tokyo (JP)

( * ) Notice: Subject to any disclaimer, the term of this patent is extended or adjusted under 35 U.S.C. 154(b) by 171 days.

(21) Appl. No.: 16/986,281

(22) Filed: Aug. 6, 2020

(65) Prior Publication Data

US 2021/0059504 A1 Mar. 4, 2021

(30) Foreign Application Priority Data

Aug. 7, 2019 (JP) .................................. 2019-145796

(51) Int. Cl.
*A61B 1/00* (2006.01)
(52) U.S. Cl.
CPC ........ *A61B 1/00006* (2013.01); *A61B 1/0002* (2013.01); *A61B 1/00018* (2013.01)
(58) Field of Classification Search
CPC ............ A61B 1/00006; A61B 1/00018; A61B 1/0002
See application file for complete search history.

(56) References Cited

U.S. PATENT DOCUMENTS

| 5,740,801 A * | 4/1998 | Branson ................. G16H 20/40 600/407 |
| 7,464,236 B2 * | 12/2008 | Sano .................... G06F 11/2076 714/6.1 |
| 9,055,246 B2 * | 6/2015 | Tay ................... H01L 27/14603 |
| 2003/0093503 A1 * | 5/2003 | Yamaki .................. G16Z 99/00 709/220 |

(Continued)

FOREIGN PATENT DOCUMENTS

JP 07-303652 A 11/1995

*Primary Examiner* — Timothy J Neal
*Assistant Examiner* — William B Chou
(74) *Attorney, Agent, or Firm* — XSENSUS LLP

(57) ABSTRACT

A signal processing apparatus relays communication of control signals between a controller and a plurality of processing modules, and includes: a communication device configured to perform communication of the control signals with the plurality of processing modules; a plurality of first storages provided respectively to correspond to the plurality of processing modules, the plurality of first storages being configured to store the control signals written by the controller; a second storage configured to store: address information indicating each communication address assigned to each of the plurality of processing modules; and correspondence information indicating correspondence relationships between the plurality of first storages and a plurality of module-side storages respectively included in the plurality of processing modules; and a synchronization processor configured to synchronize the plurality of first storages with the plurality of corresponding module-side storages via the communication device based on the address information and the correspondence information.

10 Claims, 18 Drawing Sheets

(56) References Cited

U.S. PATENT DOCUMENTS

| | | | |
|---|---|---|---|
| 2003/0159001 A1* | 8/2003 | Chalmer | G06F 3/0601 |
| | | | 711/119 |
| 2005/0060506 A1* | 3/2005 | Higaki | G06F 3/0683 |
| | | | 714/E11.12 |
| 2007/0168461 A1* | 7/2007 | Moore | G16H 10/60 |
| | | | 709/217 |
| 2012/0124309 A1* | 5/2012 | Watanabe | G06F 3/0647 |
| | | | 711/E12.103 |
| 2015/0089179 A1* | 3/2015 | Kurita | G06F 3/067 |
| | | | 711/170 |
| 2017/0180682 A1* | 6/2017 | Mizuno | H04N 9/76 |
| 2019/0268508 A1* | 8/2019 | Ono | H04N 5/217 |
| 2019/0273846 A1* | 9/2019 | Shiraishi | H04N 5/247 |
| 2020/0100830 A1* | 4/2020 | Henderson | H04L 63/0227 |
| 2020/0107710 A1* | 4/2020 | Duckett, III | A61B 1/00105 |
| 2020/0297202 A1* | 9/2020 | Tashiro | A61B 1/045 |
| 2020/0405414 A1* | 12/2020 | Shelton, IV | A61B 34/37 |

\* cited by examiner

SIGNAL PROCESSING APPARATUS

This application claims priority from Japanese Application No. 2019-145796, filed on Aug. 7, 2019, the contents of which are incorporated by reference herein in its entirety.

BACKGROUND

The present disclosure relates to a signal processing apparatus.

In the related art, a medical endoscope system that performs communication of control signals between a controller and a plurality of processing modules has been known (for example, refer to JP-A-H7-303652).

In the medical endoscope system described in JP-A-H7-303652, a controller (system controller) and a plurality of processing modules (including a relationship between an endoscope camera device, a light source device, a centralized display panel, a centralized control panel, a high-frequency cautery, a pneumoperitoneum device, and a central processing unit (CPU) in the system controller, and a processing module) are connected in a one-to-one relationship. The controller is caused to function as a master, and the plurality of processing modules are centrally controlled by the controller.

SUMMARY

As in the medical endoscope system described in JP-A-H7-303652, in a case where a configuration in which a controller and a plurality of processing modules are connected in a one-to-one manner is adopted, when the number of constituents of a plurality of processing modules is changed, it is necessary to change the control specification of the controller, which is a problem.

Therefore, there is a demand for a technique that may improve convenience without changing the control specification of the controller even in a case where the number of constituents of a plurality of processing modules is changed.

There is a need for a signal processing apparatus capable of improving convenience.

According to one aspect of the present disclosure, there is provided a signal processing apparatus for relaying communication of control signals between a controller and a plurality of processing modules, the signal processing apparatus including: a communication device configured to perform communication of the control signals with the plurality of processing modules; a plurality of first storages provided respectively to correspond to the plurality of processing modules, the plurality of first storages being configured to store the control signals written by the controller; a second storage configured to store: address information indicating each communication address assigned to each of the plurality of processing modules; and correspondence information indicating correspondence relationships between the plurality of first storages and a plurality of module-side storages respectively included in the plurality of processing modules; and a synchronization processor configured to synchronize the plurality of first storages with the plurality of corresponding module-side storages via the communication device based on the address information and the correspondence information.

DETAILED DESCRIPTION

Figure 1:
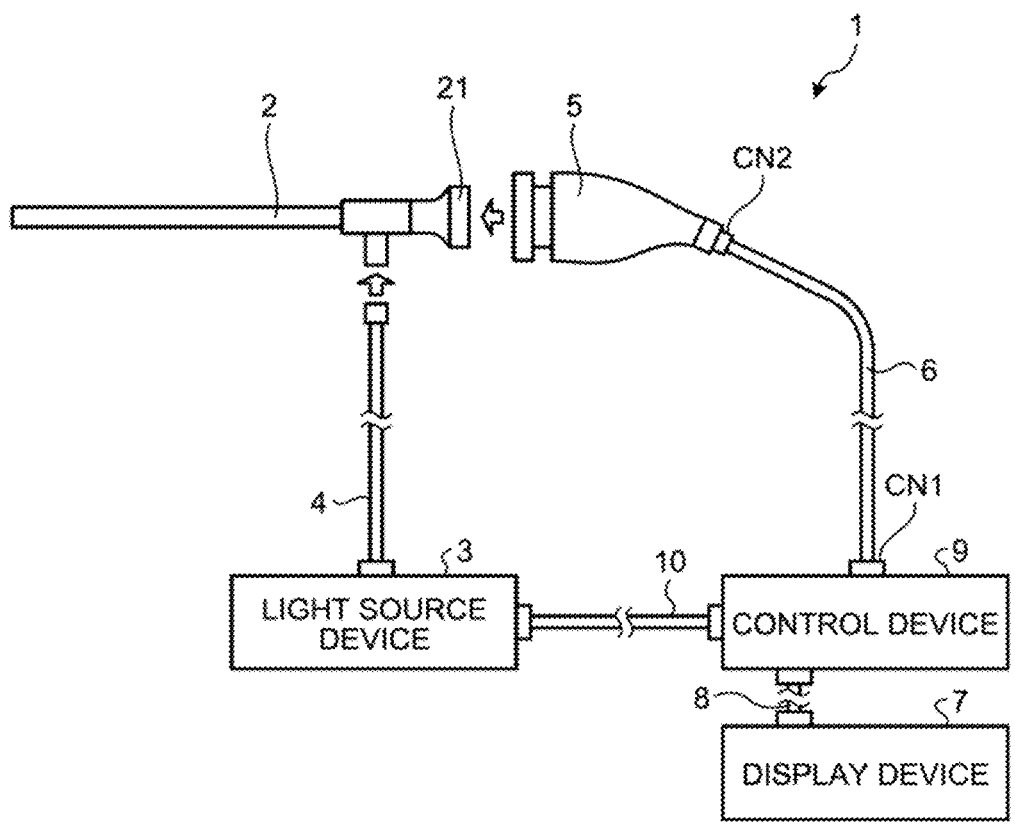
FIG. 1 is a diagram illustrating a schematic configuration of a medical observation system according to an embodiment.

Hereinafter, embodiments for implementing the disclosure (hereinafter, embodiments) will be described with reference to the drawings. The disclosure is not limited by the embodiments described below. Further, in the description of the drawings, the same portions are denoted by the same reference numerals.

Schematic Configuration of Medical Observation System

FIG. 1 is a diagram illustrating a schematic configuration of a medical observation system 1 according to an embodiment.

The medical observation system 1 is used in the medical field and is a system for observing a subject such as a living body. As illustrated in FIG. 1, the medical observation system 1 includes an insertion portion 2, a light source device 3, a light guide 4, a camera head 5, a first transmission cable 6, a display device 7, a second transmission cable 8, a control device 9, and a third transmission cable 10.

In the present embodiment, the insertion portion 2 is composed of a rigid endoscope. That is, the insertion portion 2 has an elongated shape which is rigid as a whole or of which a part is flexible and the other part is rigid, and is inserted into a living body. An optical system that is configured by using one or a plurality of lenses and that condenses light (subject image) from the inside of the living body is provided in the insertion portion 2. The light source device 3 is connected to one end of the light guide 4, and supplies light for illuminating the inside of the living body to one end of the light guide 4 under the control of the control device 9.

In addition, in the present embodiment, the light source device 3 is configured separately from the control device 9, but the disclosure is not limited to this, and a configuration in which the light source device 3 is provided inside the control device 9 may be adopted.

The light guide 4 has one end detachably connected to the light source device 3 and the other end detachably connected to the insertion portion 2. Then, the light guide 4 transmits the light supplied from the light source device 3 from one end to the other end, and supplies the light to the insertion portion 2. The light supplied to the insertion portion 2 is emitted from a distal end of the insertion portion 2, and is irradiated to the inside of the living body. The light (subject image) that is irradiated to the inside of the living body and reflected in the living body is condensed by the optical system in the insertion portion 2.

The camera head 5 is detachably connected to a proximal end (eyepiece portion 21 (FIG. 1)) of the insertion portion 2. Then, under the control of the control device 9, the camera head 5 captures the subject image condensed by the insertion portion 2, and outputs an image signal (RAW signal) obtained by the imaging. The image signal is, for example, an image signal of 4K or higher.

The first transmission cable 6 has one end detachably connected to the control device 9 via a connector CN1 (FIG. 1) and the other end detachably connected to the camera head 5 via a connector CN2 (FIG. 1). Then, the first transmission cable 6 transmits the image signal and the like output from the camera head 5 to the control device 9, and transmits the control signal, the synchronization signal, the clock, the power, and the like output from the control device 9 to the camera head 5.

The transmission of the image signal and the like from the camera head 5 to the control device 9 via the first transmission cable 6 may be transmission of the image signal and the like by an optical signal or an electric signal. The same applies to the transmission of the control signal, the synchronization signal, and the clock from the control device 9 to the camera head 5 via the first transmission cable 6.

The display device 7 is composed of a display using liquid crystal or organic electro luminescence (EL), and displays an image based on a video signal from the control device 9 under the control of the control device 9.

The second transmission cable 8 has one end detachably connected to the display device 7 and the other end detachably connected to the control device 9. Then, the second transmission cable 8 transmits the video signal processed by the control device 9 to the display device 7.

The control device 9 is configured to include a CPU, a field-programmable gate array (FPGA), and the like, and comprehensively controls the operations of the light source device 3, the camera head 5, and the display device 7.

For example, the control device 9 generates a video signal by performing a predetermined process on the image signal acquired from the camera head 5 via the first transmission cable 6. Further, the control device 9 outputs the video signal to the display device 7 via the second transmission cable 8. Then, the display device 7 displays an image based on the video signal. Further, the control device 9 outputs a control signal and the like to the light source device 3 and the camera head 5.

The third transmission cable 10 has one end detachably connected to the light source device 3 and the other end detachably connected to the control device 9. Then, the third transmission cable 10 transmits the control signal and the like from the control device 9 to the light source device 3.

Configuration of Control Device Next, the configuration of the control device 9 will be described.

Hereinafter, the main part of the disclosure will be mainly described as the control device 9.

Figure 2:
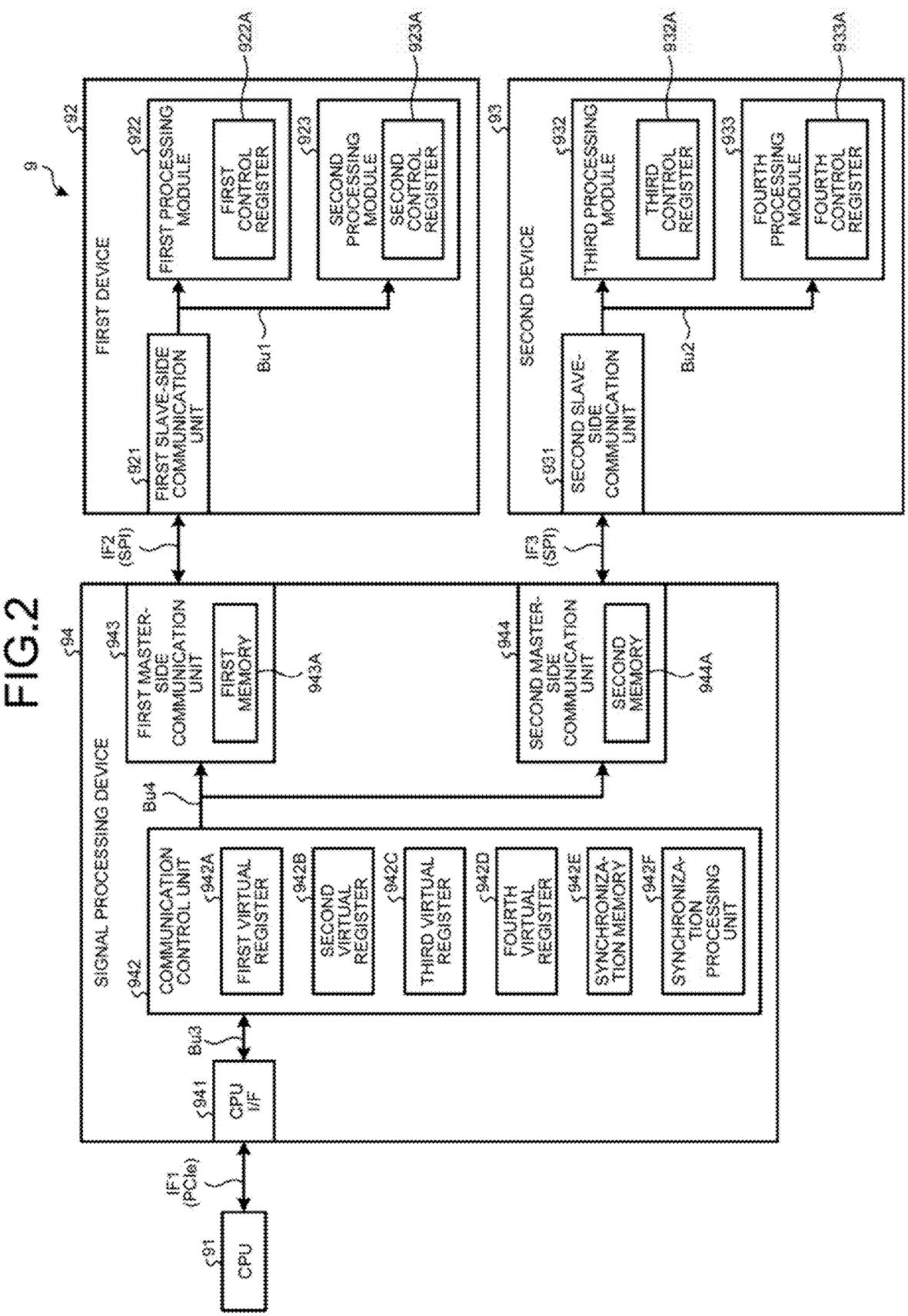
FIG. 2 is a block diagram illustrating a configuration of a control device.

FIG. 2 is a block diagram illustrating a configuration of the control device 9.

As illustrated in FIG. 2, the control device 9 has a configuration in which a CPU 91, first and second devices 92 and 93, and a signal processing apparatus 94 are connected using first to third interfaces IF1 to IF3.

Here, the first interface IF1 that connects the CPU 91 and the signal processing apparatus 94 is an interface that has data transfer speed (communication speed) faster than that of the second interface IF2 that connects the first device 92 and the signal processing apparatus 94, and the third interface IF3 that connects the second device 93 and the signal processing apparatus 94. In the present embodiment, PCI EXPRESS (PCIe (registered trademark)) is adopted as the first interface IF1. Moreover, the Serial Peripheral Interface (SPI) is adopted as the second and third interfaces IF2 and IF3.

The CPU 91 corresponds to the controller according to the disclosure. The CPU 91 is a part that comprehensively controls the entire operation of the medical observation system 1, and outputs each control signal that defines a process to be executed by each of a plurality of control targets (in the present embodiment, first to fourth processing modules 922, 923, 932, and 933 to be described later). In the present embodiment, the CPU 91 is composed of a CPU that performs communication by the PCIe standard.

Each of the first and second devices 92 and 93 is a device that executes a specific process under the control of the CPU 91. As the first and second devices 92 and 93, a device that generates a video signal by performing various image processing such as development processing, noise reduction, color correction, color enhancement, and edge enhancement on the image signal acquired from the camera head 5, a device that controls (dimming control and the like) the operation of the light source device 3, and the like are exemplified. The first and second devices 92 and 93 are not limited to the devices built in the control device 9, but may be devices built in peripheral devices of the control device 9. For example, the first and second devices 92 and 93 may be devices that are built in the camera head 5 and that control the operation of the camera head 5 (operation of imaging elements, operation of the optical system, and the like).

Each of the first and second devices 92 and 93 described above is configured by an FPGA that is a programmable logic device that constructs a logic circuit based on configuration data stored in a memory (not illustrated).

Then, as illustrated in FIG. 2, the first device 92 includes a first slave-side communication unit 921, and the first and second processing modules 922 and 923 that are connected to the first slave-side communication unit 921 via a bus Bu1.

In the present embodiment, the bus Bu1 is composed of an AXI bus.

The first slave-side communication unit 921 is connected to the signal processing apparatus 94 via the second interface IF2. Then, the first slave-side communication unit 921 converts (protocol-converts) the control signal (SPI standard in the present embodiment) received from the signal processing apparatus 94 into data (AXI standard in the present embodiment) that may be processed inside the first device 92 via the second interface IF2. Further, the first slave-side communication unit 921 converts (protocol-converts) data (AXI standard in the present embodiment) output from the first and second processing modules 922 and 923 into a control signal according to the communication standard (SPI standard in the present embodiment) of the second interface IF2, and transmits the control signal to the signal processing apparatus 94 via the second interface IF2.

The first and second processing modules 922 and 923 correspond to the processing module according to the disclosure. Each of the first and second processing modules 922 and 923 executes a specific process according to the control signal which is output from the CPU 91, follows the route of the first interface IF1 to the signal processing apparatus 94 to the second interface IF2 to the first slave-side communication unit 921 to the bus Bu1, and is stored in internal first and second control registers 922A and 923A (FIG. 2). The first and second control registers 922A and 923A correspond to a module-side storage unit according to the disclosure.

The second device 93 has the same configuration as that of the first device 92 except that the specific process executed by the second device 93 is different from that executed by the first device 92. That is, as illustrated in FIG. 2, the second device 93 includes a second slave-side communication unit 931, the third and fourth processing modules 932 and 933 (including third and fourth control registers 932A and 933A), and a bus Bu2 as with the first slave-side communication unit 921, the first and second processing modules 922 and 923 (including the first and second control registers 922A and 923A), and the bus Bu1 in the first device 92. The third and fourth control registers 932A and 933A correspond to the module-side storage unit according to the disclosure.

The signal processing apparatus 94 relays communication of control signals between the CPU 91 and the first to fourth processing modules 922, 923, 932, and 933. In the present embodiment, the signal processing apparatus 94 is configured by an FPGA as with the first and second devices 92 and 93. Then, as illustrated in FIG. 2, the signal processing apparatus 94 includes a CPU I/F 941, a communication control unit 942 connected to the CPU I/F 941 via a bus Bu3, and first and second master-side communication units 943 and 944 connected to the communication control unit 942 via a bus Bu4.

In the present embodiment, the buses Bu3 and Bu4 are composed of AXI buses.

The CPU I/F 941 is connected to the CPU 91 via the first interface IF1. Then, the CPU I/F 941 converts (protocol-converts) the control signal (PCIe standard in the present embodiment) received from the CPU 91 into data (AXI standard in the present embodiment) that may be processed inside the signal processing apparatus 94 via the first interface IF1. Further, the CPU I/F 941 converts (protocol-converts) data (AXI standard in the present embodiment) output from the communication control unit 942 into a control signal according to the communication standard (PCIe standard in the present embodiment) of the first interface IF1, and transmits the control signal to the CPU 91 via the first interface IF1.

As illustrated in FIG. 2, the communication control unit 942 includes first to fourth virtual registers 942A to 942D, a synchronization memory 942E, and a synchronization processing unit 942F.

The first to fourth virtual registers 942A to 942D correspond to a first storage unit according to the disclosure. These first to fourth virtual registers 942A to 942D are respectively provided corresponding to the first to fourth processing modules 922, 923, 932, and 933, and are virtualized registers of the first to fourth control registers 922A, 923A, 932A, and 933A. Then, each control signal (data converted by the CPU I/F 941) output from the CPU 91 is written in each of the first to fourth virtual registers 942A to 942D.

The synchronization memory 942E corresponds to a second storage unit according to the disclosure. The synchronization memory 942E stores address information and correspondence information used in a synchronization process executed by the synchronization processing unit 942F.

The address information is information indicating each communication address assigned to each of the first to fourth processing modules 922, 923, 932, and 933. The correspondence information is information indicating correspondence relationships between the first to fourth virtual registers 942A to 942D and the first to fourth control registers 922A, 923A, 932A, and 933A. Specifically, the correspondence information describes that the first virtual register 942A and the first control register 922A correspond to each other, the second virtual register 942B and the second control register 923A correspond to each other, the third virtual register 942C and the third control register 932A correspond to each other, and the fourth virtual register 942D and the fourth control register 933A correspond to each other.

The synchronization processing unit 942F executes a synchronization process for synchronizing the first to fourth virtual registers 942A to 942D with the corresponding first to fourth control registers 922A, 923A, 932A, and 933A via the first and second master-side communication units 943 and 944 based on the address information and the correspondence information stored in the synchronization memory 942E. Specifically, the synchronization processing unit 942F synchronizes the first virtual register 942A with the first control register 922A with each other, synchronizes the second virtual register 942B with the second control register 923A, synchronizes the third virtual register 942C with the third control register 932A, and synchronizes the fourth virtual register 942D with the fourth control register 933A.

A specific example of the synchronization process will be described later.

The first master-side communication unit 943 corresponds to a communication unit according to the disclosure. The first master-side communication unit 943 is connected to the first slave-side communication unit 921 via the second interface IF2. Further, the first master-side communication unit 943 converts (protocol-converts) data (AXI standard in the present embodiment) output from the communication control unit 942 (first and second virtual registers 942A and 942B) into a control signal according to the communication standard (SPI standard in the present embodiment) of the second interface IF2, and transmits the control signal to the first slave-side communication unit 921 via the second interface IF2 under the control of the communication control unit 942. Further, the first master-side communication unit 943 converts (protocol-converts) the control signal (SPI standard in the present embodiment) received from the first slave-side communication unit 921 into data (AXI standard in the present embodiment) that may be processed inside the signal processing apparatus 94 via the second interface IF2.

The first master-side communication unit 943 described above has a first memory 943A that temporarily stores data (control signal), as illustrated in FIG. 2. The first memory 943A corresponds to a third storage unit according to the disclosure.

The second master-side communication unit 944 corresponds to the communication unit according to the disclosure. The second master-side communication unit 944 is connected to the second slave-side communication unit 931 via the third interface IF3. Further, the second master-side communication unit 944 converts (protocol-converts) data (AXI standard in the present embodiment) output from the communication control unit 942 (third and fourth virtual registers 942C and 942D) into a control signal according to the communication standard (SPI standard in the present embodiment) of the third interface IF3, and transmits the control signal to the second slave-side communication unit 931 via the third interface IF3 under the control of the communication control unit 942. Further, the second master-side communication unit 944 converts (protocol-converts) the control signal (SPI standard in the present embodiment) received from the second slave-side communication unit 931 into data (AXI standard in the present embodiment) that may be processed inside the signal processing apparatus 94 via the third interface IF3.

The second master-side communication unit 944 described above has a second memory 944A that temporarily stores data (control signal), as illustrated in FIG. 2. The second memory 944A corresponds to the third storage unit according to the disclosure.

Specific Example of Synchronization Process

Next, a specific example of the synchronization process executed by the synchronization processing unit 942F will be described.

In the following, as the synchronization process, a writing process of writing pieces of data stored in the first to fourth virtual registers 942A to 942D to the first to fourth control registers 922A, 923A, 932A, and 933A, respectively, and a reading process of reading the pieces of data stored in the first to fourth control registers 922A, 923A, 932A, and 933A and writing the pieces of data to the first to fourth virtual registers 942A to 942D, respectively, will be sequentially described.

When the first and second devices 92 and 93 are activated, the synchronization processing unit 942F receives a ready signal indicating the activation from each of the first and second devices 92 and 93 via the second and third interfaces IF2 and IF3. Then, after the ready signal is received from the first and second devices 92 and 93, the synchronization processing unit 942F executes the writing process and the reading process described below.

Writing Process

FIGS. 3 to 10 are diagrams describing the writing process. Specifically, FIG. 3 to FIG. 10 illustrate respective states in which the writing process is being performed in chronological order. In addition, in FIG. 3 to FIG. 10, for convenience of description, respective pieces of data exchanged between the first to fourth virtual registers 942A to 942D and the first to fourth control registers 922A, 923A, 932A, and 933A are represented by diagonal lines and dots. Further, in FIG. 3 to FIG. 10, the data exchanged between the first virtual register 942A and the first control register 922A (control signal which is output from the CPU 91 and defines the process executed by the first processing module 922) is defined as "Reg(1)". Hereinafter, this data will be referred to as "Reg (1)" data. Further, in FIG. 3 to FIG. 10, the data exchanged between the second virtual register 942B and the second control register 923A (control signal which is output from the CPU 91 and defines the process executed by the second processing module 923) is defined as "Reg(2)". Hereinafter, this data will be referred to as "Reg(2)" data. Further, in FIG. 3 to FIG. 10, the data exchanged between the third virtual register 942C and the third control register 932A (control signal which is output from the CPU 91 and defines the process executed by the third processing module 932) is defined as "Reg(3)". Hereinafter, this data will be referred to as "Reg(3)" data. Further, in FIG. 3 to FIG. 10, the data exchanged between the fourth virtual register 942D and the fourth control register 933A (control signal which is output from the CPU 91 and defines the process executed by the fourth processing module 933) is defined as "Reg(4)". Hereinafter, this data will be referred to as "Reg(4)" data. Further, in FIGS. 3 to 10, in the communication control unit 942, the synchronization memory 942E and the synchronization processing unit 942F are not illustrated for convenience of description.

In the following, the description is made such that the synchronization processing unit 942F writes the pieces of data respectively stored in the first to fourth virtual registers 942A to 942D to the first to fourth control registers 922A, 923A, 932A, and 933A in order of "Reg(1)" data, "Reg(3)" data, "Reg(2)" data, and "Reg(4)" data. Note that the writing order is not limited to this, and the writing may be performed in any other order.

First, the synchronization processing unit 942F refers to the correspondence information stored in the synchronization memory 942E. Then, the synchronization processing unit 942F recognizes that the control register corresponding to the first virtual register 942A is the first control register 922A based on the correspondence information. The synchronization processing unit 942F also refers to the address information stored in the synchronization memory 942E. Then, the synchronization processing unit 942F recognizes the communication address of the first processing module 922 including the first control register 922A.

Figure 3:
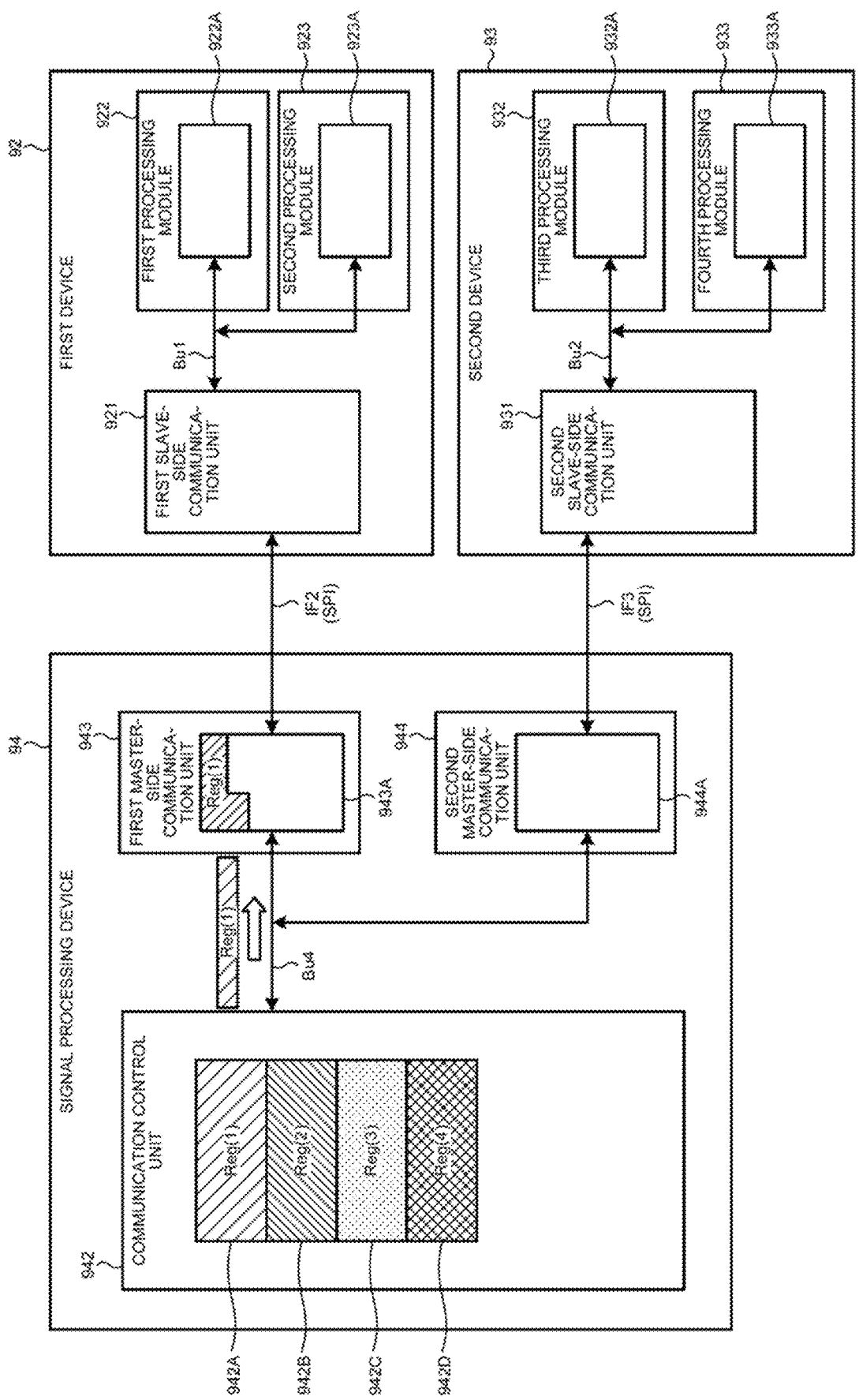
FIG. 3 is a diagram describing a writing process.

Then, as illustrated in FIG. 3, the synchronization processing unit 942F transfers the "Reg(1)" data stored in the first virtual register 942A to the first master-side communication unit 943 via the bus Bu4 based on the recognized communication address. As a result, the "Reg(1)" data is stored in the first memory 943A.

Figure 4:
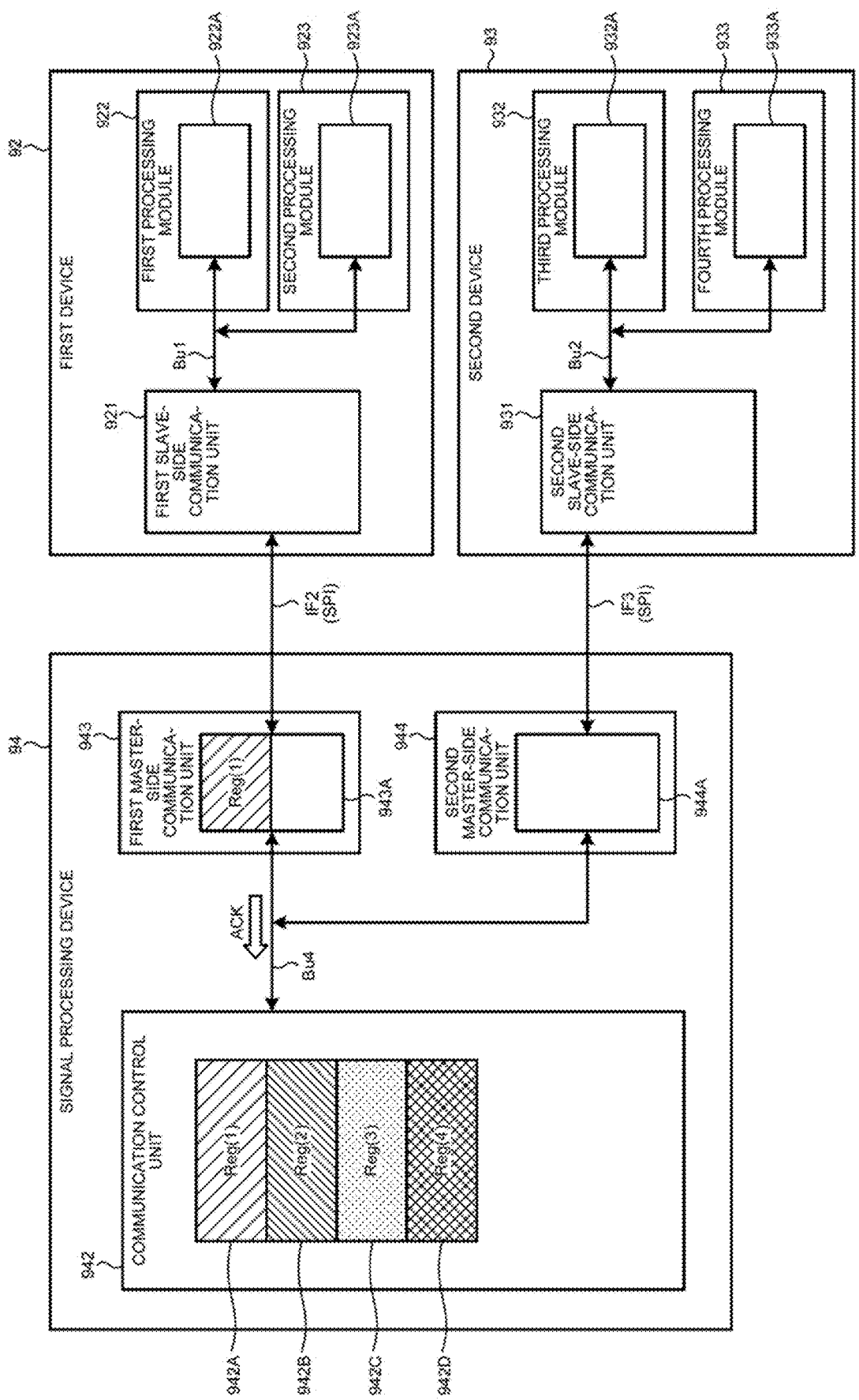
FIG. 4 is a diagram describing a writing process.
Figure 5:
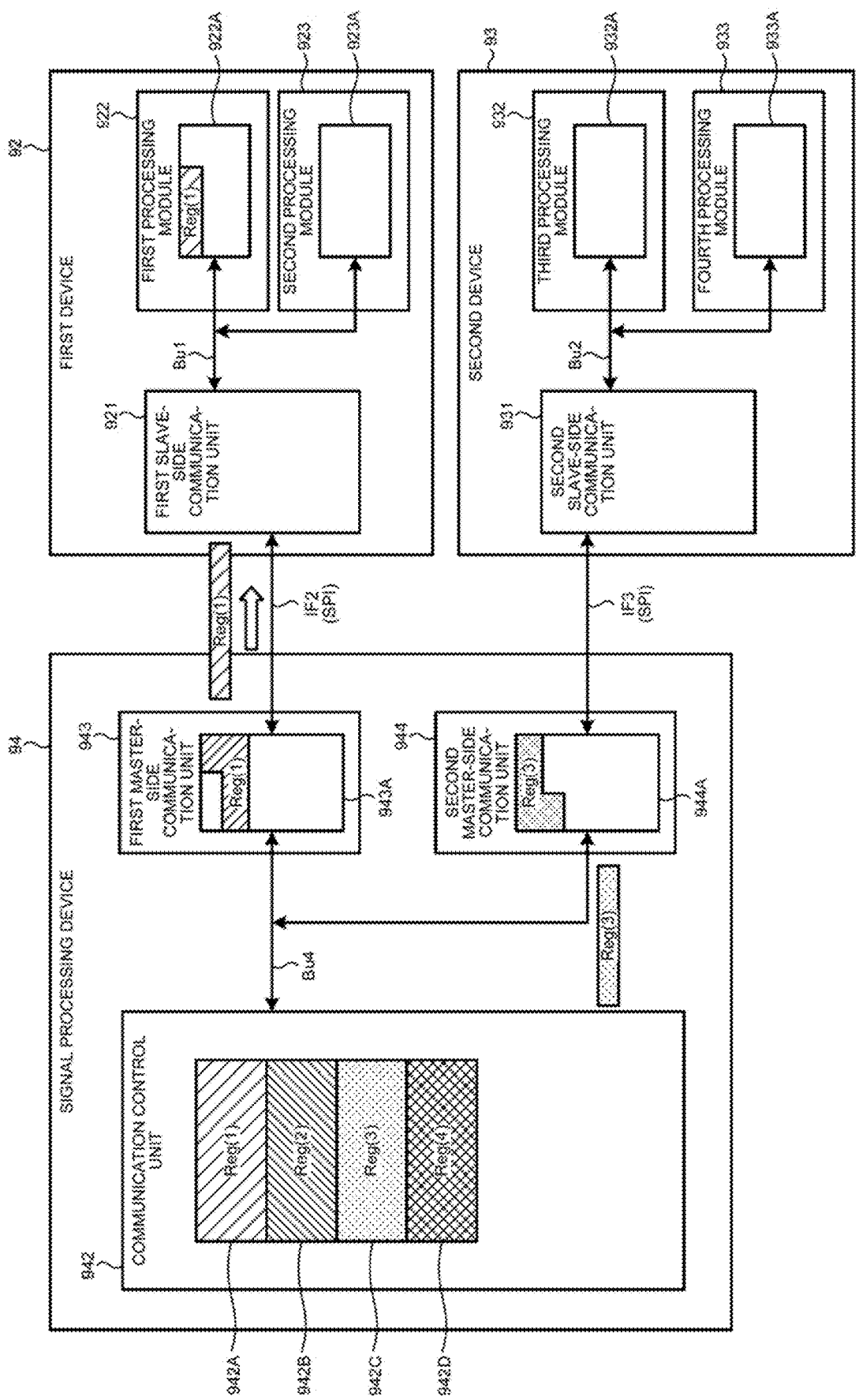
FIG. 5 is a diagram describing a writing process.

When the transfer of all of the pieces of the "Reg(1)" data from the first virtual register 942A to the first master-side communication unit 943 is completed, the synchronization processing unit 942F receives an ACK signal from the first master-side communication unit 943 via the bus Bu4 as illustrated in FIG. 4. After that, as illustrated in FIG. 5, the first master-side communication unit 943 transmits the "Reg (1)" data stored in the first memory 943A to the first device 92 via the second interface IF2. Then, the "Reg(1)" data is written to the first control register 922A by following the route of the second interface IF2 to the first slave-side communication unit 921 to the bus Bu1. That is, after transmitting the ACK signal to the synchronization processing unit 942F, the first master-side communication unit 943 transmits the data to the first device 92 without the control of the synchronization processing unit 942F. There is also a method in which the synchronization processing unit 942F controls the operation of the first master-side communication unit 943 in response to the reception of the ACK signal. Furthermore, the first master-side communication unit 943 may start to transmit the data to the first device 92 before transmitting the ACK signal to the synchronization processing unit 942F.

In addition, the synchronization processing unit 942F executes the following process in parallel with the transmission of the "Reg(1)" data from the first master-side communication unit 943 to the first device 92.

That is, the synchronization processing unit 942F refers to the correspondence information stored in the synchronization memory 942E. Then, the synchronization processing unit 942F recognizes that the control register corresponding to the third virtual register 942C is the third control register 932A based on the correspondence information. The synchronization processing unit 942F also refers to the address information stored in the synchronization memory 942E. Then, the synchronization processing unit 942F recognizes the communication address of the third processing module 932 including the third control register 932A.

Then, as illustrated in FIG. 5, the synchronization processing unit 942F transfers the "Reg(3)" data stored in the third virtual register 942C to the second master-side communication unit 944 via the bus Bu4 based on the recognized communication address. As a result, the "Reg(3)" data is stored in the second memory 944A.

Figure 6:
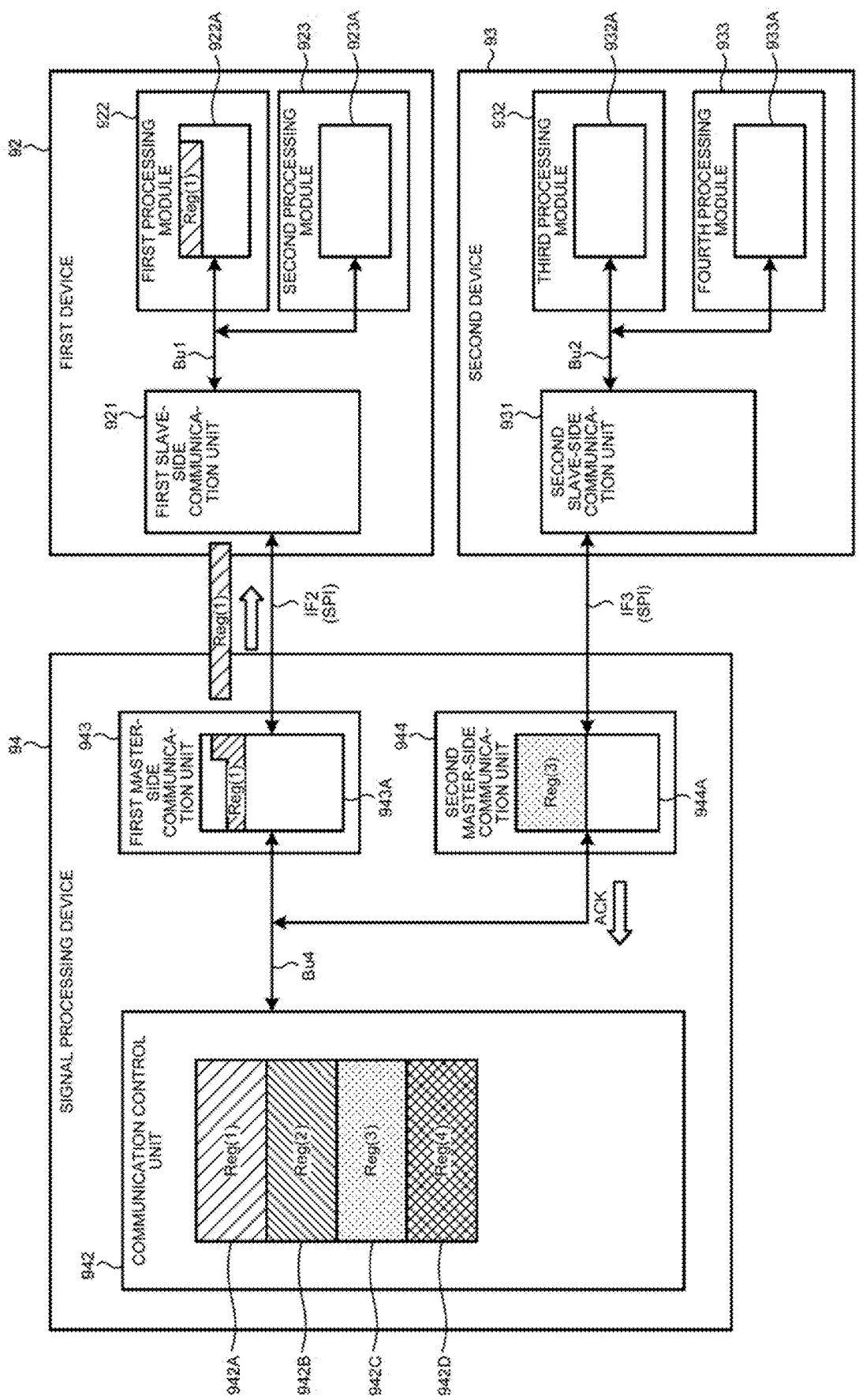
FIG. 6 is a diagram describing a writing process.
Figure 7:
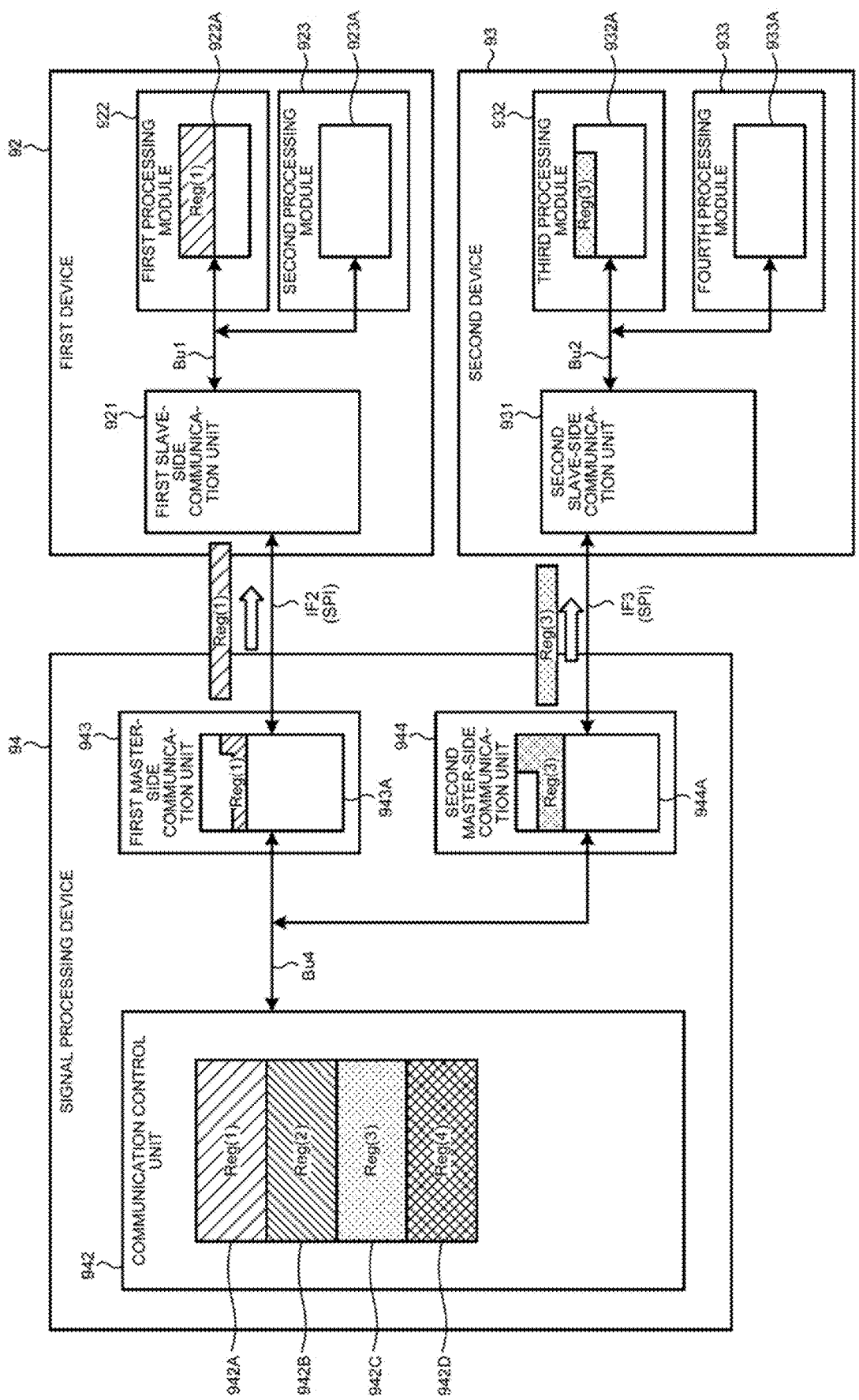
FIG. 7 is a diagram describing a writing process.

When the transfer of all of the pieces of the "Reg(3)" data from the third virtual register 942C to the second master-side communication unit 944 is completed, the synchronization processing unit 942F receives an ACK signal from the second master-side communication unit 944 via the bus Bu4 as illustrated in FIG. 6. After that, as illustrated in FIG. 7, the second master-side communication unit 944 transmits the "Reg(3)" data stored in the second memory 944A to the second device 93 via the third interface IF3. Then, the "Reg(3)" data is written to the third control register 932A by following the route of the third interface IF3 to the second slave-side communication unit 931 to the bus Bu2. That is, after transmitting the ACK signal to the synchronization processing unit 942F, the second master-side communication unit 944 transmits the data to the second device 93 without the control of the synchronization processing unit 942F. There is also a method in which the synchronization processing unit 942F controls the operation of the second master-side communication unit 944 in response to the reception of the ACK signal. Furthermore, the second master-side communication unit 944 may start to transmit the data to the second device 93 before transmitting the ACK signal to the synchronization processing unit 942F.

Figure 8:
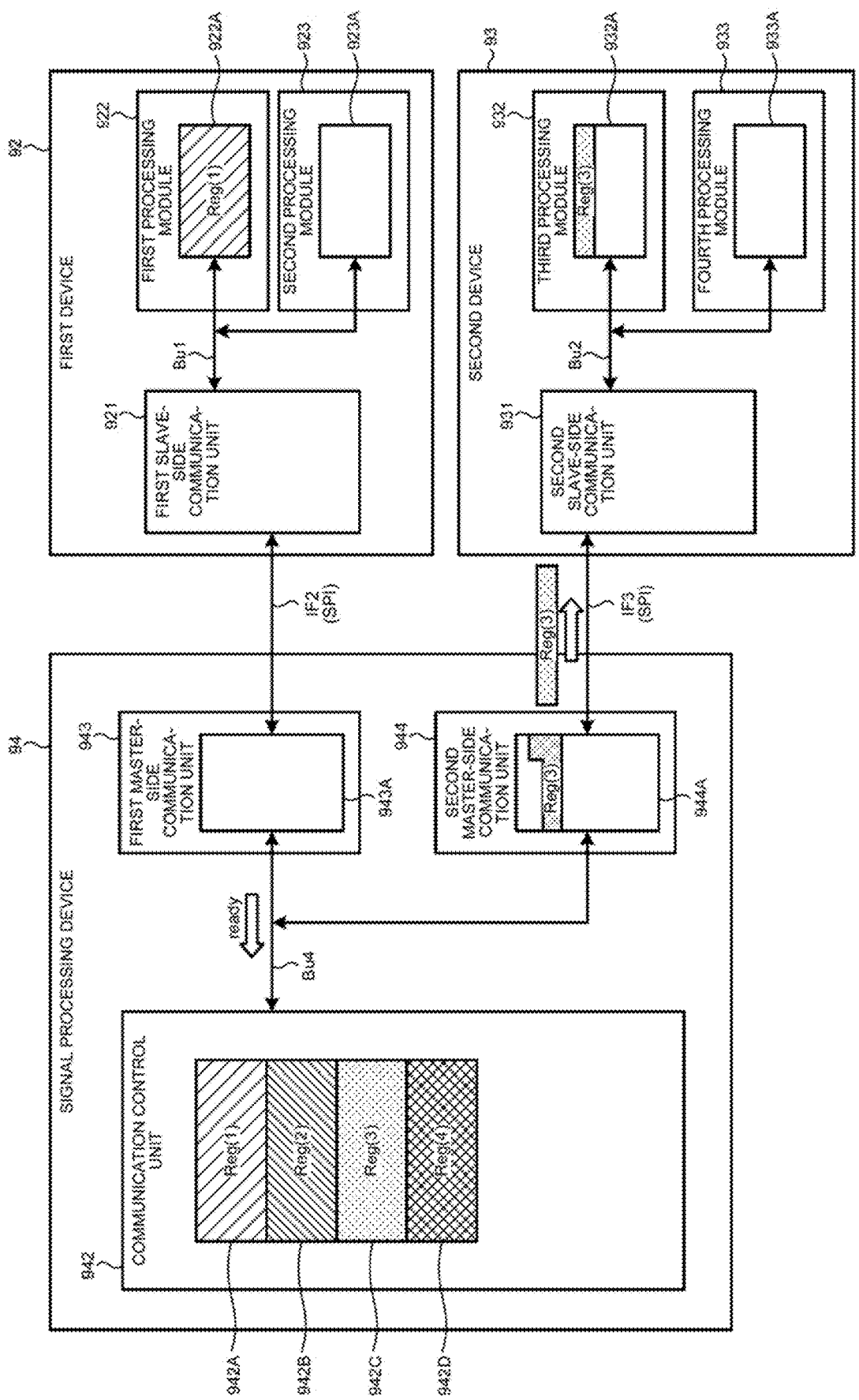
FIG. 8 is a diagram describing a writing process.

When the transfer of all of the pieces of the "Reg(1)" data from the first master-side communication unit 943 to the first device 92 is completed, the synchronization processing unit 942F receives a ready signal from the first master-side communication unit 943 via the bus Bu4 as illustrated in FIG. 8. After that, the synchronization processing unit 942F executes the following process.

That is, the correspondence information stored in the synchronization memory 942E is referred. Then, the synchronization processing unit 942F recognizes that the control register corresponding to the second virtual register 942B is the second control register 923A based on the correspondence information. The synchronization processing unit 942F also refers to the address information stored in the synchronization memory 942E. Then, the synchronization processing unit 942F recognizes the communication address of the second processing module 923 including the second control register 923A.

Figure 9:
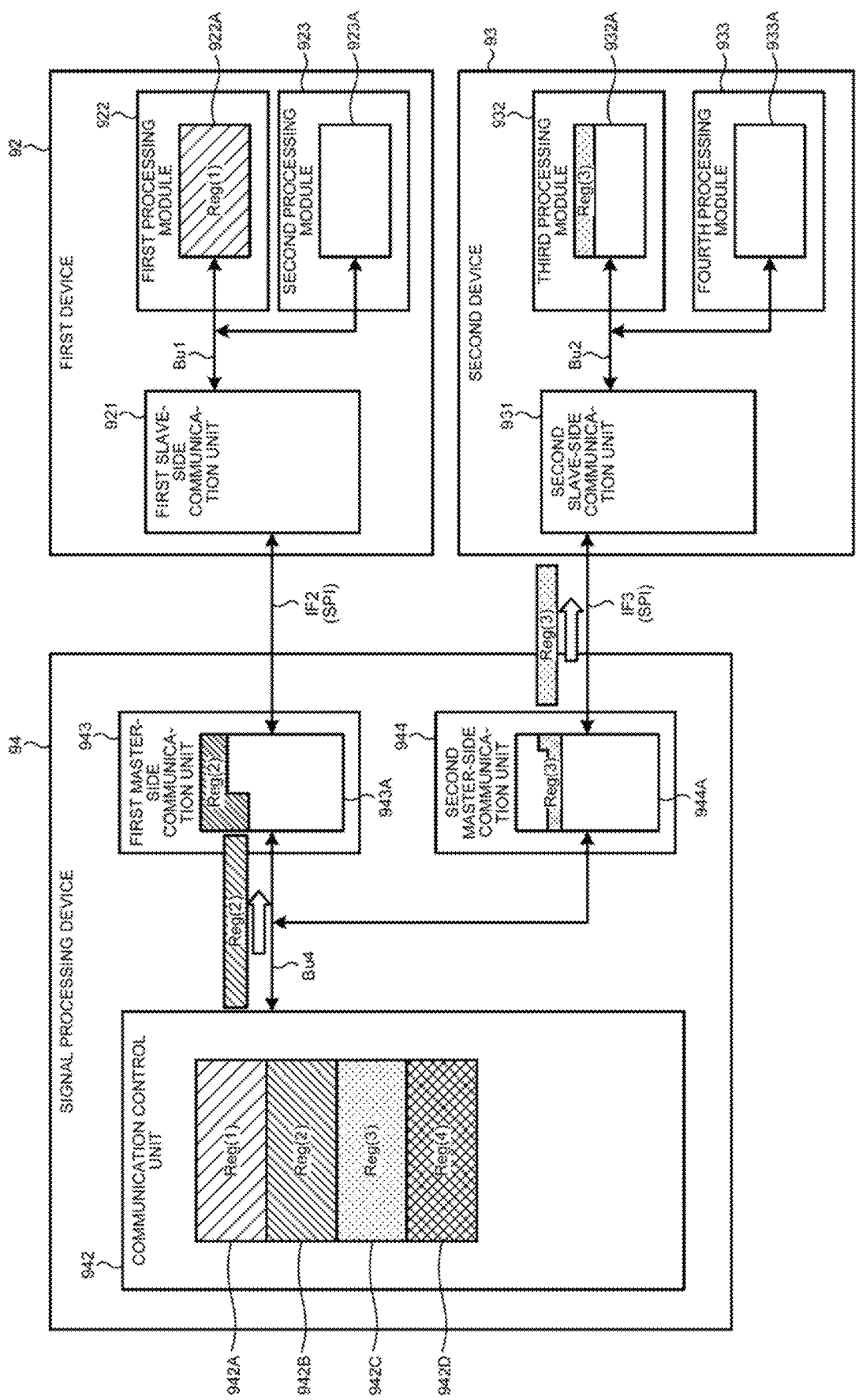
FIG. 9 is a diagram describing a writing process.

Then, as illustrated in FIG. 9, the synchronization processing unit 942F transfers the "Reg(2)" data stored in the second virtual register 942B to the first master-side communication unit 943 via the bus Bu4 based on the recognized communication address. As a result, the "Reg(2)" data is stored in the first memory 943A.

Figure 10:
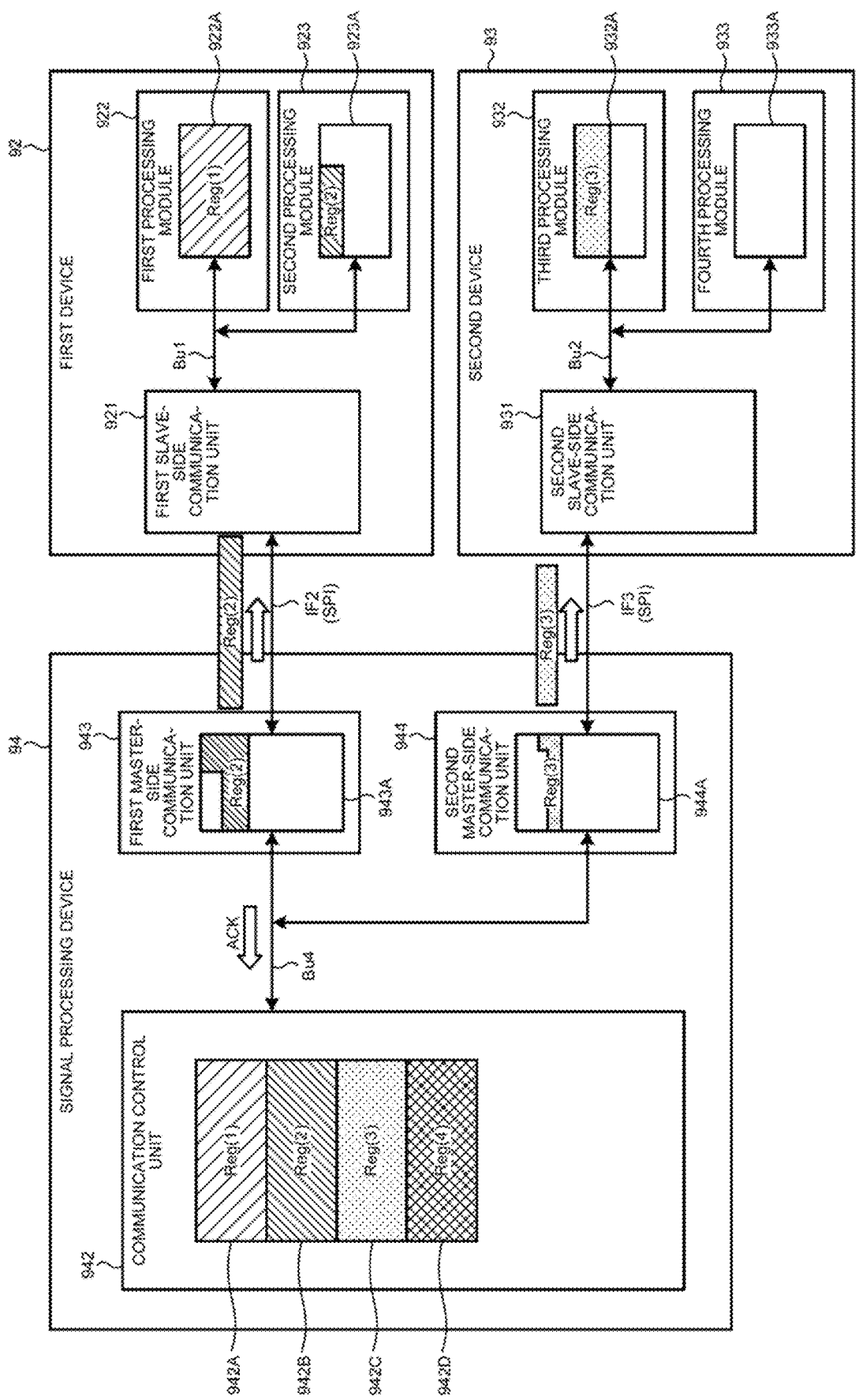
FIG. 10 is a diagram describing a writing process.

When the transfer of all of the pieces of the "Reg(2)" data from the second virtual register 942B to the first master-side communication unit 943 is completed, the synchronization processing unit 942F receives an ACK signal from the first master-side communication unit 943 via the bus Bu4 as illustrated in FIG. 10. After that, as illustrated in FIG. 10, the first master-side communication unit 943 transmits the "Reg(2)" data stored in the first memory 943A to the first device 92 via the second interface IF2. Then, the "Reg(2)" data is written to the second control register 923A by following the route of the second interface IF2 to the first slave-side communication unit 921 to the bus Bu1. That is, after transmitting the ACK signal to the synchronization processing unit 942F, the first master-side communication unit 943 transmits the data to the first device 92 without the control of the synchronization processing unit 942F. There is also a method in which the synchronization processing unit 942F controls the operation of the first master-side communication unit 943 in response to the reception of the ACK signal. Furthermore, the first master-side communication unit 943 may start to transmit the data to the first device 92 before transmitting the ACK signal to the synchronization processing unit 942F.

Note that the writing of the "Reg(4)" data stored in the fourth virtual register 942D to the fourth control register 933A is executed after the transfer of all of the pieces of the "Reg(3)" data from the second master-side communication unit 944 to the second device 93 is completed and the synchronization processing unit 942F receives a ready signal from the second master-side communication unit 944 via the bus Bu4.

Reading Process

FIGS. 11 to 18 are diagrams describing the reading process. Specifically, FIG. 11 to FIG. 18 illustrate respective states in which the reading process is being performed in chronological order. Note that in FIGS. 11 to 18, respective pieces of data exchanged between the first to fourth virtual registers 942A to 942D and the first to fourth control registers 922A, 923A, 932A, and 933A are represented in the same manner as in FIG. 3 to FIG. 10. Further, in FIGS. 11 to 18, in the communication control unit 942, the synchronization memory 942E and the synchronization processing unit 942F are not illustrated for convenience of description.

In the following, the description is made such that the synchronization processing unit 942F reads the pieces of data respectively stored in the first to fourth control registers 922A, 923A, 932A, and 933A in order of "Reg(1)" data, "Reg(3)" data, "Reg(2)" data, and "Reg(4)" data, and writes the pieces of data to the first to fourth virtual registers 942A to 942D. Note that the reading order is not limited to this, and the reading may be performed in any other order.

First, the synchronization processing unit 942F refers to the correspondence information stored in the synchronization memory 942E. Then, the synchronization processing unit 942F recognizes that the control register corresponding to the first virtual register 942A is the first control register 922A based on the correspondence information. The synchronization processing unit 942F also refers to the address information stored in the synchronization memory 942E. Then, the synchronization processing unit 942F recognizes the communication address of the first processing module 922 including the first control register 922A.

Figure 11:
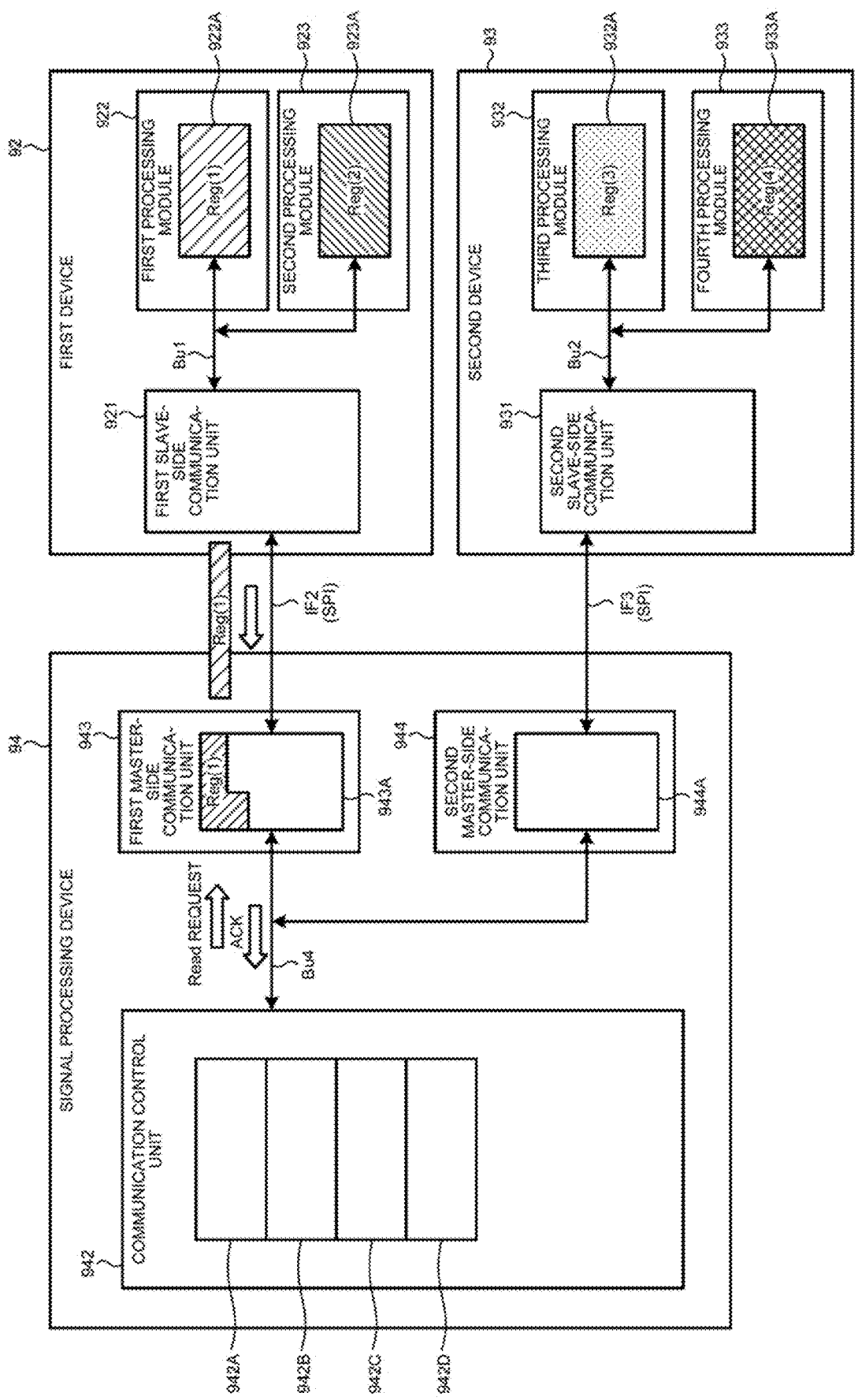
FIG. 11 is a diagram describing a reading process.

Then, as illustrated in FIG. 11, the synchronization processing unit 942F outputs a Read request signal for requesting reading of the "Reg(1)" data stored in the first control register 922A, to the first master-side communication unit 943 via the bus Bu4 based on the recognized communication address. When the Read request signal is received, the first master-side communication unit 943 outputs an ACK signal to the synchronization processing unit 942F via the bus Bu4, and transmits the Read request signal to the first device 92 via the second interface IF2. As a result, as illustrated in FIG. 11, the first processing module 922 transmits the "Reg(1)" data stored in the first control register 922A to the first master-side communication unit 943 by following the route of the bus Bu1 to the first slave-side communication unit 921 to the second interface IF2. Then, the "Reg(1)" data is stored in the first memory 943A.

After that, the synchronization processing unit 942F refers to the correspondence information stored in the synchronization memory 942E. Then, the synchronization processing unit 942F recognizes that the control register corresponding to the third virtual register 942C is the third control register 932A based on the correspondence information. The synchronization processing unit 942F also refers to the address information stored in the synchronization memory 942E. Then, the synchronization processing unit 942F recognizes the communication address of the third processing module 932 including the third control register 932A.

Figure 12:
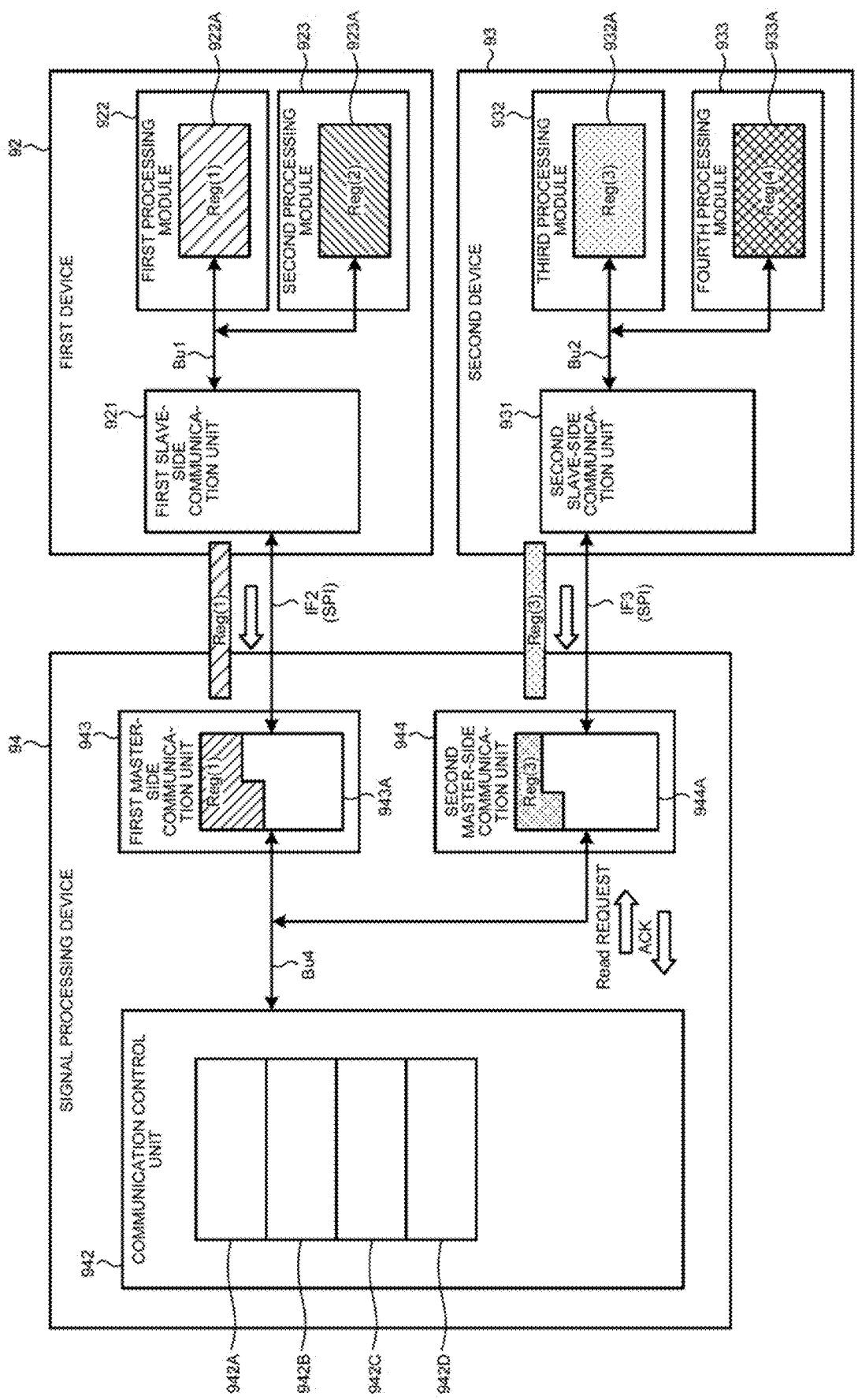
FIG. 12 is a diagram describing a reading process.

Then, as illustrated in FIG. 12, the synchronization processing unit 942F outputs a Read request signal for requesting reading of the "Reg(3)" data stored in the third control register 932A, to the second master-side communication unit 944 via the bus Bu4 based on the recognized communication address. When the Read request signal is received, the second master-side communication unit 944 outputs an ACK signal to the synchronization processing unit 942F via the bus Bu4, and transmits the Read request signal to the second device 93 via the third interface IF3. As a result, as illustrated in FIG. 12, the third processing module 932 transmits the "Reg(3)" data stored in the third control register 932A to the second master-side communication unit 944 by following the route of the bus Bu2 to the second slave-side communication unit 931 to the third interface IF3. Then, the "Reg(3)" data is stored in the second memory 944A.

Figure 13:
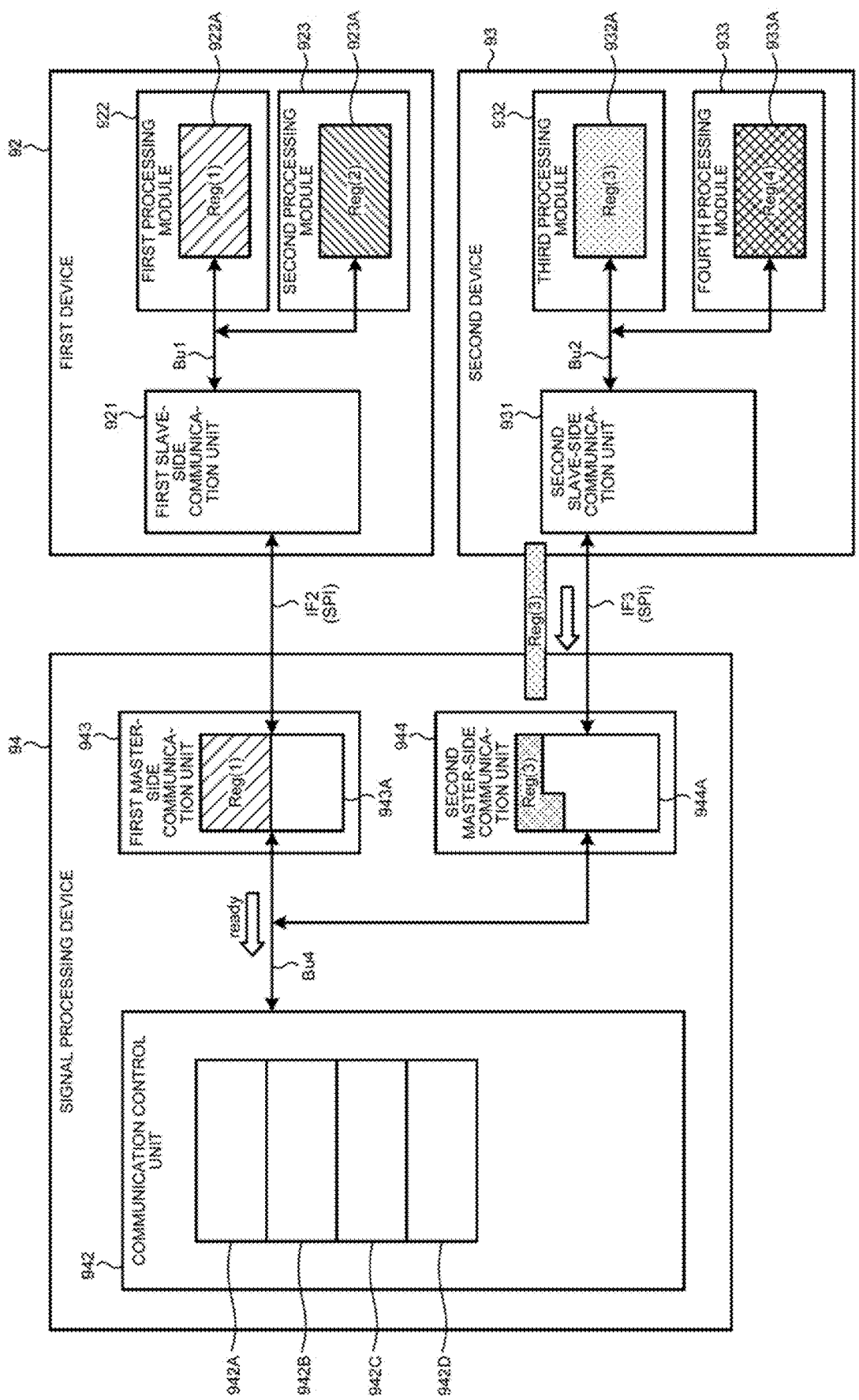
FIG. 13 is a diagram describing a reading process.
Figure 14:
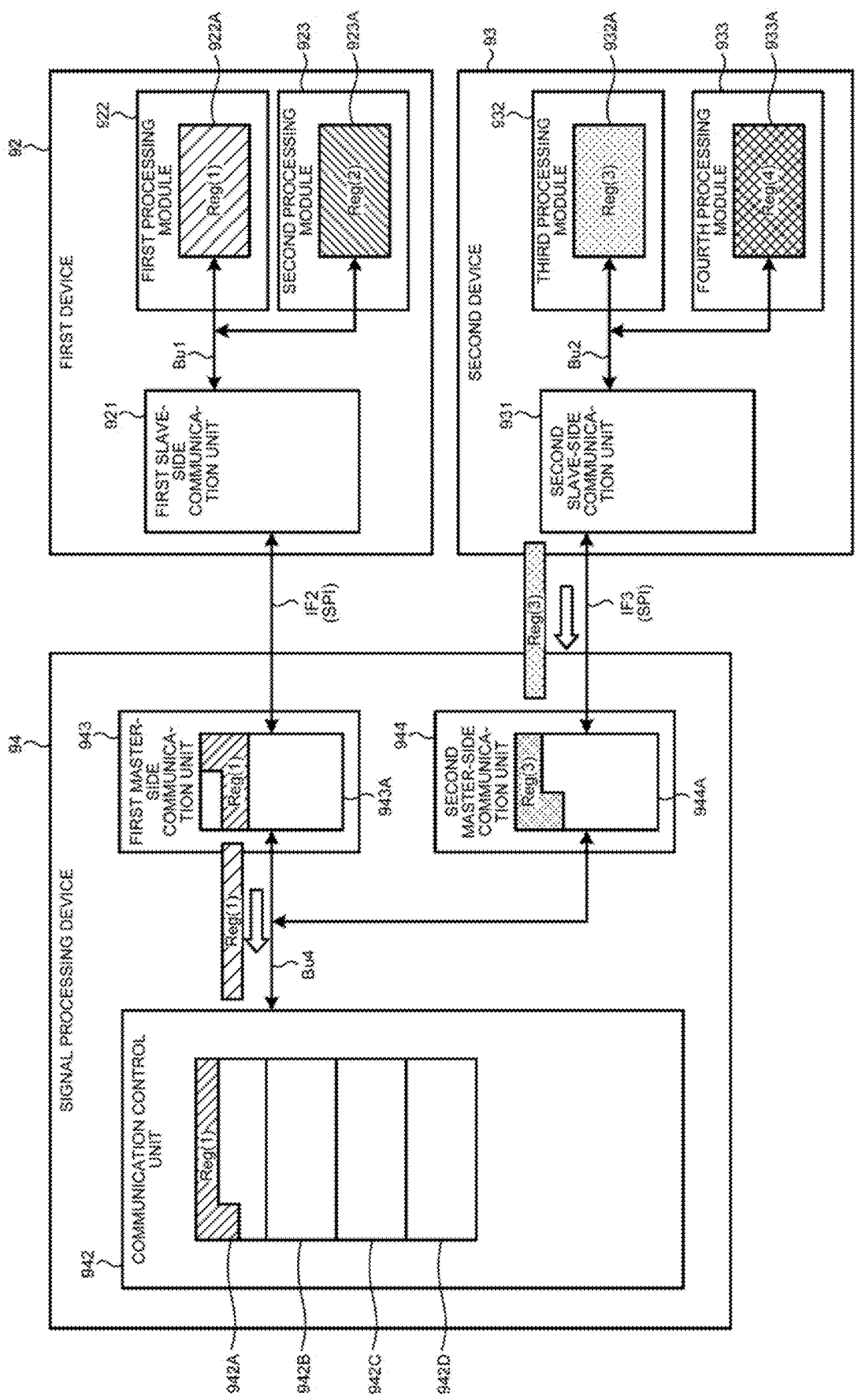
FIG. 14 is a diagram describing a reading process.

When the transfer of all of the pieces of the "Reg(1)" data from the first control register 922A to the first master-side communication unit 943 is completed, the synchronization processing unit 942F receives a ready signal from the first master-side communication unit 943 via the bus Bu4 as illustrated in FIG. 13. As illustrated in FIG. 14, the synchronization processing unit 942F transfers (writes) the "Reg(1)" data stored in the first memory 943A to the first virtual register 942A via the bus Bu4 in response to the reception of the ready signal.

When the transfer of all of the pieces of the "Reg(1)" data from the first memory 943A to the first virtual register 942A is completed, the synchronization processing unit 942F executes the following process.

That is, the synchronization processing unit 942F refers to the correspondence information stored in the synchronization memory 942E. Then, the synchronization processing unit 942F recognizes that the control register corresponding to the second virtual register 942B is the second control register 923A based on the correspondence information. The synchronization processing unit 942F also refers to the address information stored in the synchronization memory 942E. Then, the synchronization processing unit 942F recognizes the communication address of the second processing module 923 including the second control register 923A.

Figure 15:
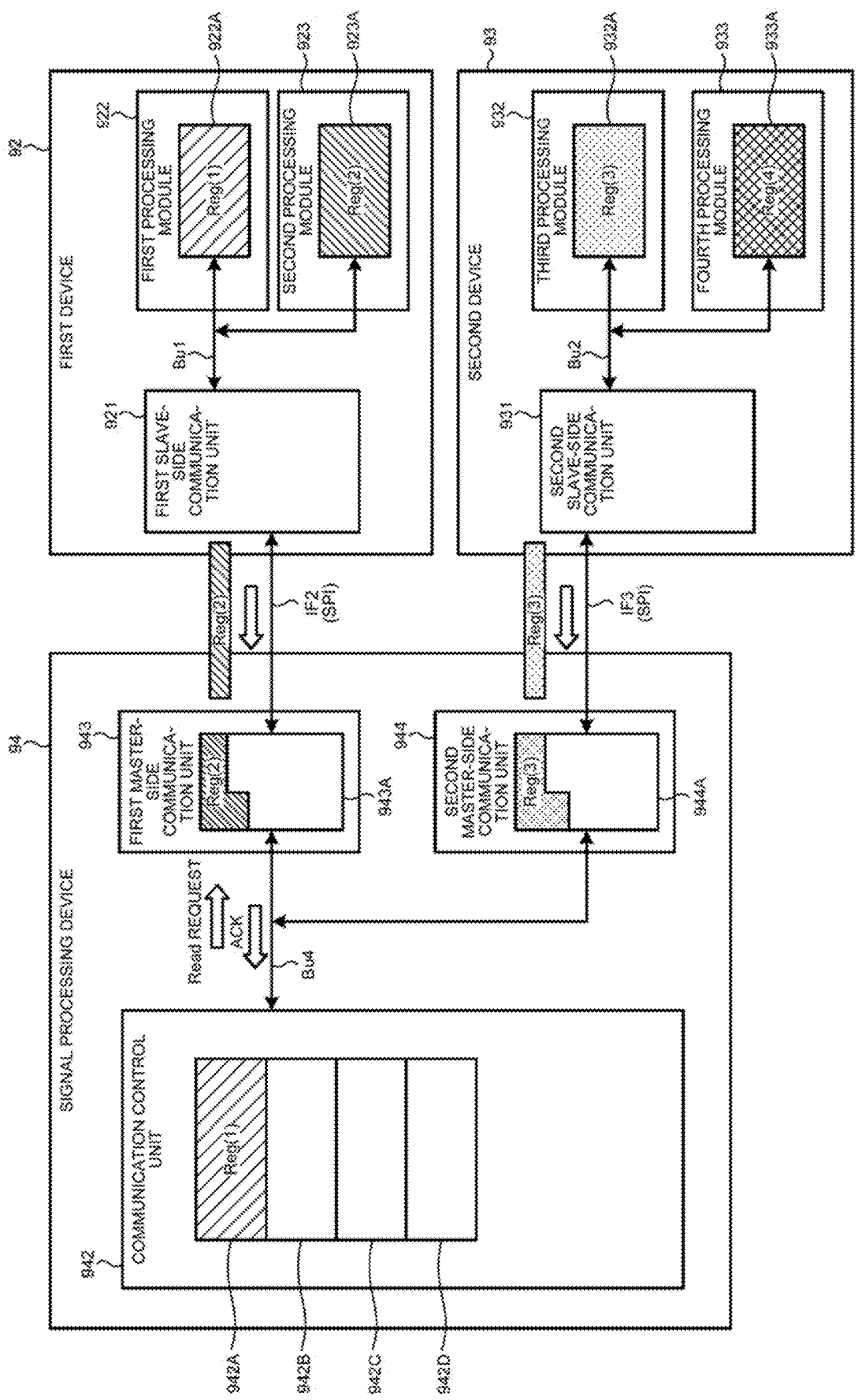
FIG. 15 is a diagram describing a reading process.

Then, as illustrated in FIG. 15, the synchronization processing unit 942F outputs a Read request signal for requesting reading of the "Reg(2)" data stored in the second control register 923A, to the first master-side communication unit 943 via the bus Bu4 based on the recognized communication address. When the Read request signal is received, the first master-side communication unit 943 outputs an ACK signal to the synchronization processing unit 942F via the bus Bu4, and transmits the Read request signal to the first device 92 via the second interface IF2. As a result, as illustrated in FIG. 15, the second processing module 923 transmits the "Reg(2)" data stored in the second control register 923A to the first master-side communication unit 943 by following the route of the bus Bu1 to the first slave-side communication unit 921 to the second interface IF2. Then, the "Reg(2)" data is stored in the first memory 943A.

Figure 16:
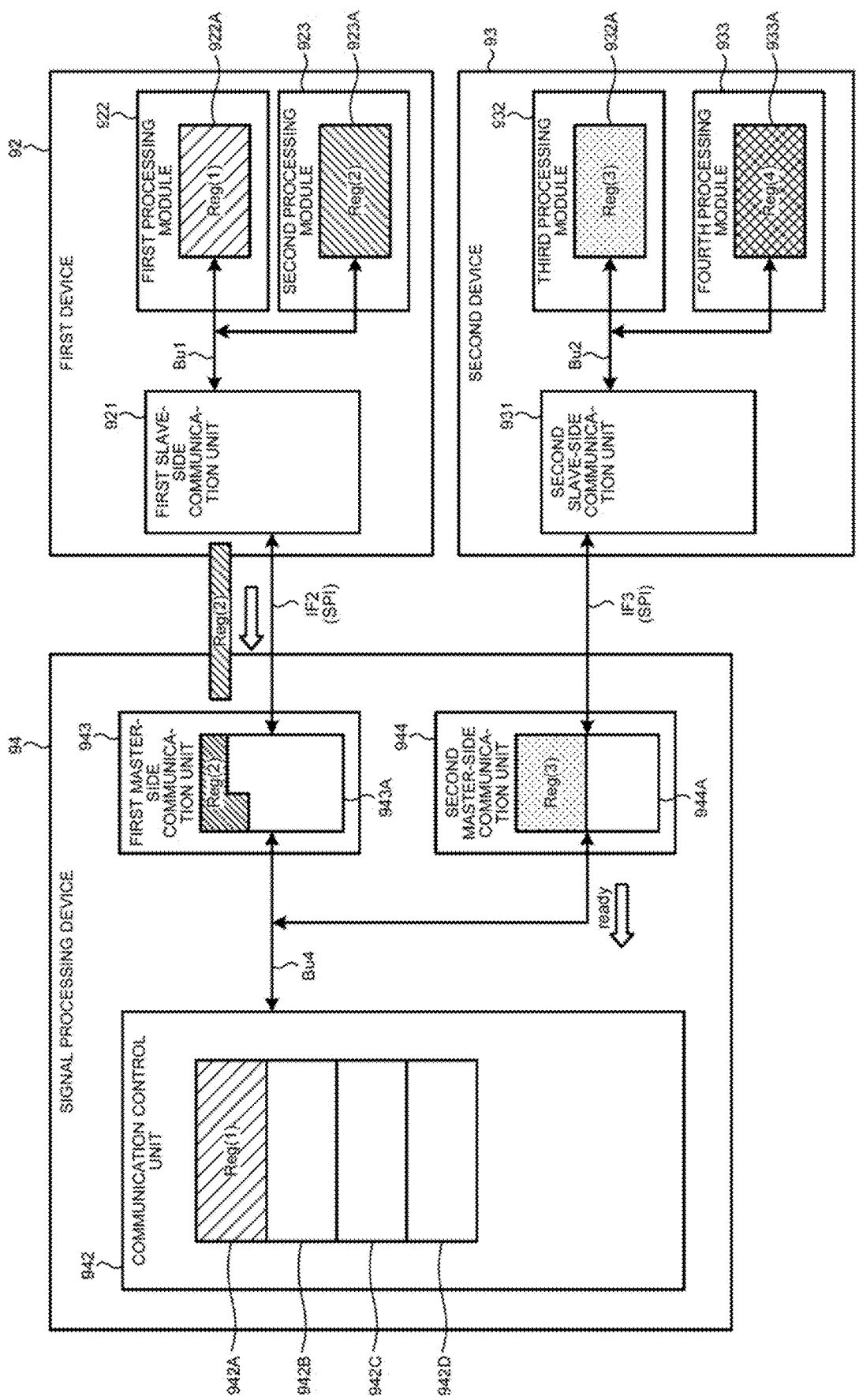
FIG. 16 is a diagram describing a reading process.
Figure 17:
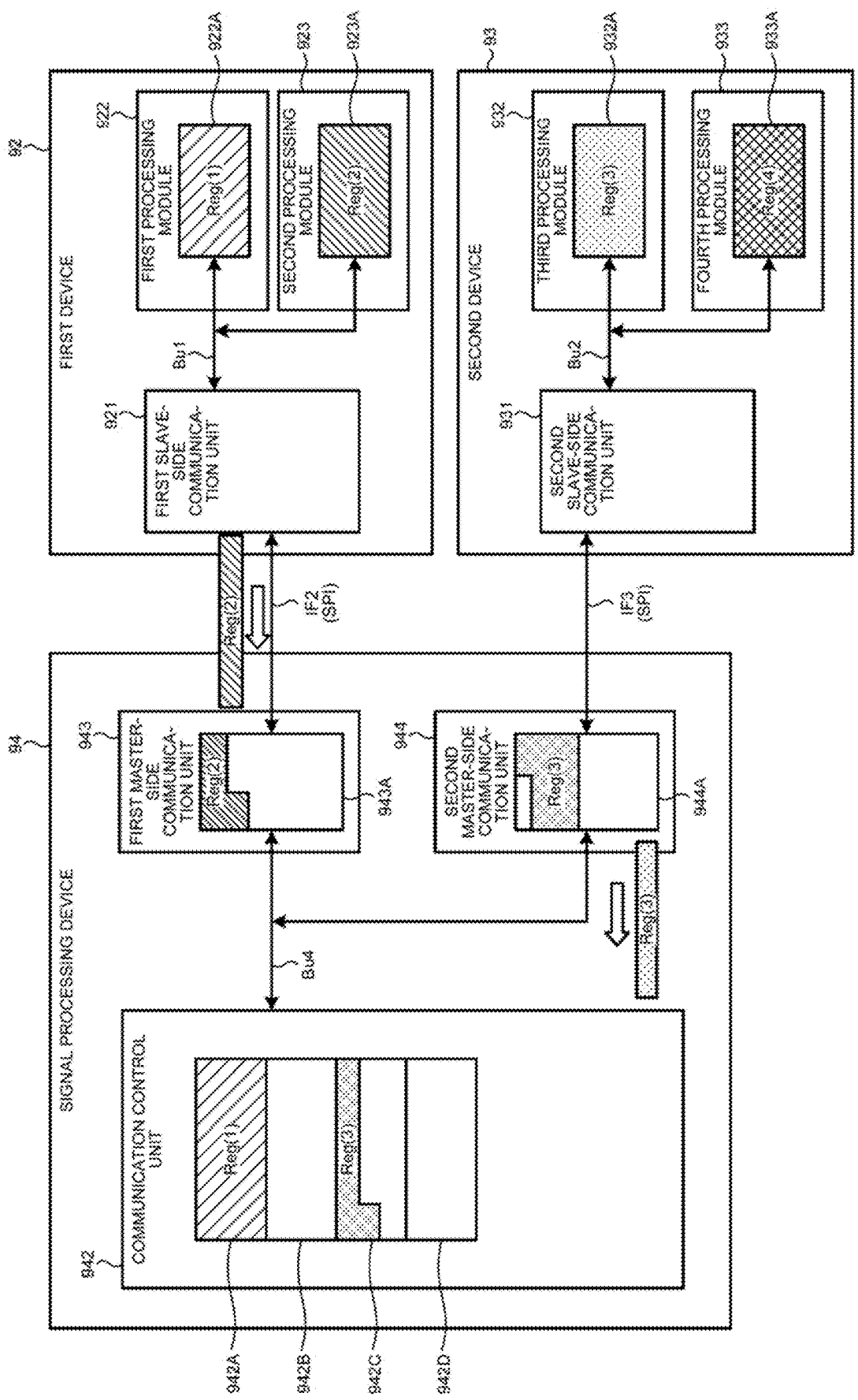
FIG. 17 is a diagram describing a reading process.

When the transfer of all of the pieces of the "Reg(3)" data from the third control register 932A to the second master-side communication unit 944 is completed, the synchronization processing unit 942F receives a ready signal from the second master-side communication unit 944 via the bus Bu4 as illustrated in FIG. 16. As illustrated in FIG. 17, the synchronization processing unit 942F transfers (writes) the "Reg(3)" data stored in the second memory 944A to the third virtual register 942C via the bus Bu4 in response to the reception of the ready signal.

When the transfer of all of the pieces of the "Reg(3)" data from the second memory 944A to the third virtual register 942C is completed, the synchronization processing unit 942F executes the following process.

That is, the synchronization processing unit 942F refers to the correspondence information stored in the synchronization memory 942E. Then, the synchronization processing unit 942F recognizes that the control register corresponding to the fourth virtual register 942D is the fourth control register 933A based on the correspondence information. The synchronization processing unit 942F also refers to the address information stored in the synchronization memory 942E. Then, the synchronization processing unit 942F recognizes the communication address of the fourth processing module 933 including the fourth control register 933A.

Figure 18:
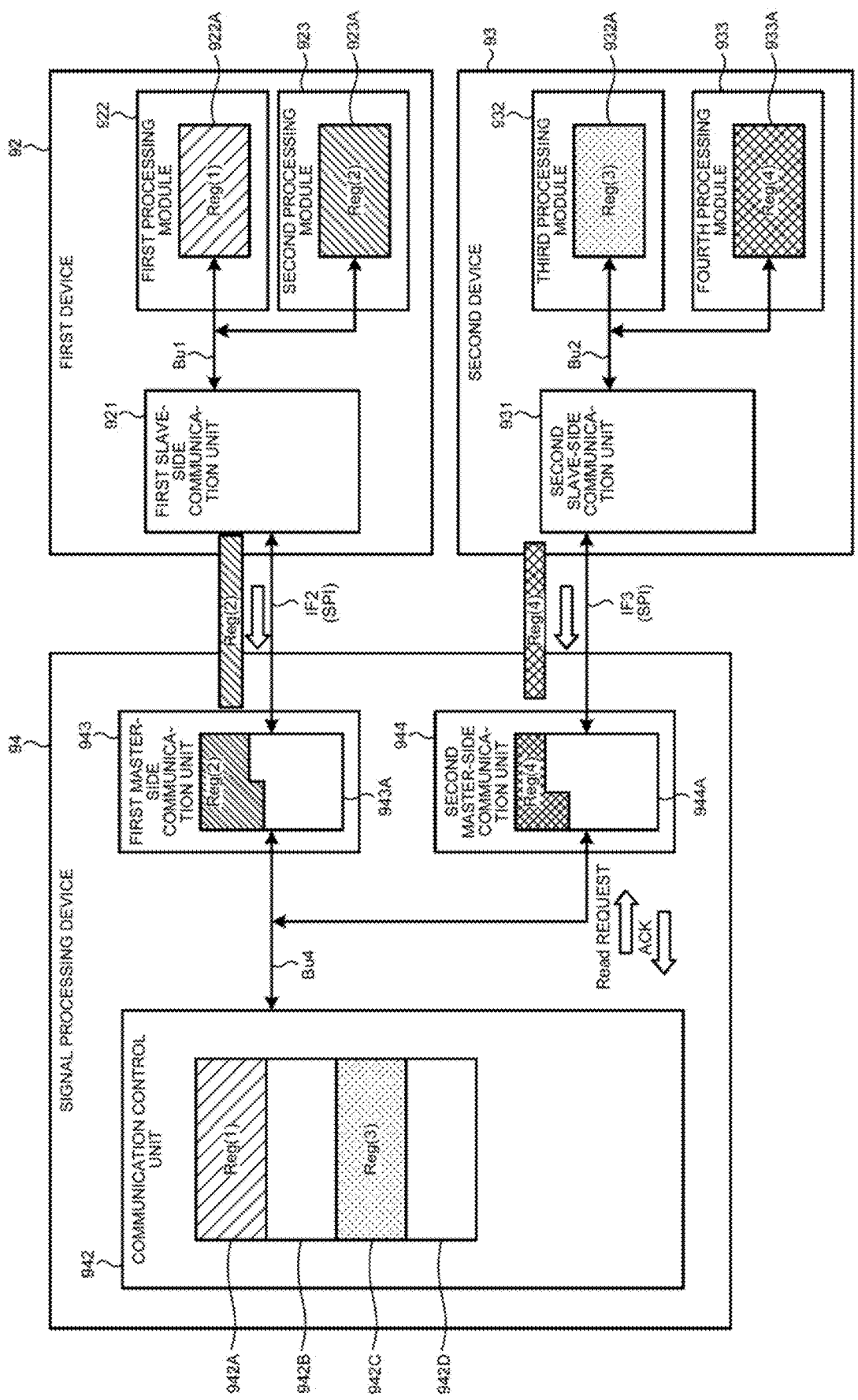
FIG. 18 is a diagram describing a reading process.

Then, as illustrated in FIG. 18, the synchronization processing unit 942F outputs a Read request signal for requesting reading of the "Reg(4)" data stored in the fourth control register 933A, to the second master-side communication unit 944 via the bus Bu4 based on the recognized communication address. When the Read request signal is received, the second master-side communication unit 944 outputs an ACK signal to the synchronization processing unit 942F via the bus Bu4, and transmits the Read request signal to the second device 93 via the third interface IF3. As a result, as illustrated in FIG. 18, the fourth processing module 933 transmits the "Reg(4)" data stored in the fourth control register 933A to the second master-side communication unit 944 by following the route of the bus Bu2 to the second slave-side communication unit 931 to the third interface IF3. Then, the "Reg(4)" data is stored in the second memory 944A.

After that, by repeating the same process as above, the "Reg(2)" data stored in the first memory 943A is transferred (written) to the second virtual register 942B, and the "Reg (4)" data stored in the second memory 944A is transferred (written) to the fourth virtual register 942D.

According to the present embodiment described above, the following effects may be obtained.

The signal processing apparatus 94 according to the present embodiment includes the first and second master-side communication units 943 and 944, the first to fourth virtual registers 942A to 942D, the synchronization memory 942E, and the synchronization processing unit 942F.

That is, in the signal processing apparatus 94, the first to fourth virtual registers 942A to 942D which are virtualized registers of the first to fourth control registers 922A, 923A, 932A, and 933A are integrated. Therefore, the CPU 91 may control all of the operations of the first to fourth processing modules 922, 923, 932, and 933 by only writing the "Reg (1)" to "Reg(4)" data to the first to fourth virtual registers 942A to 942D.

In a case where the number of constituents of a plurality of processing modules controlled by the CPU 91 is changed, it is possible to deal with the change of the number of constituents by changing the address information and the correspondence information stored in the synchronization memory 942E, and thus it is not necessary to change the control specification of the CPU 91.

Therefore, with the signal processing apparatus 94 according to the present embodiment, it is possible to improve convenience.

Further, in the signal processing apparatus 94 according to the present embodiment, a plurality of communication units (two first and second master-side communication units 943 and 944) according to the disclosure are provided.

Therefore, it is possible to perform communication between the signal processing apparatus 94 and the first and second devices 92 and 93 in parallel, and to improve the communication efficiency. As a result, it is possible to shorten the communication time of the entire system.

By the way, it is assumed that the first master-side communication unit 943 is not provided with the above-described first memory 943A. In this case, when the "Reg(1)" data stored in the first virtual register 942A is written to the first control register 922A, since the bus Bu4 is occupied for the transfer of the "Reg(1)" data from the first virtual register 942A to the first master-side communication unit 943, it is not possible to transmit the "Reg(1)" data and the "Reg(3)" or "Reg(4)" data in parallel to the first and second devices 92 and 93. Similarly, when the "Reg(2)" data stored in the second virtual register 942B is written to the second control register 923A, it is not possible to transmit the "Reg(2)" data and "Reg(3)" or "Reg(4)" data in parallel to the first and second devices 92 and 93.

Similarly, even in a case where the second master-side communication unit 944 is not provided with the above-described second memory 944A, it is not possible to transmit the "Reg(1)" or "Reg(2)" data and the "Reg(3)" or "Reg(4)" data in parallel to the first and second devices 92 and 93.

In particular, the second and third interfaces IF2 and IF3 are SPI, and the communication speed is relatively slow. For this reason, the time for occupying the bus Bu4 becomes long, and as a result, the communication time of the entire system increases.

On the other hand, in the signal processing apparatus 94 according to the present embodiment, the first and second master-side communication units 943 and 944 are provided with the above-described first and second memories 943A and 944A, respectively. Therefore, it is possible to shorten the time for occupying the bus Bu4, and to transmit the "Reg(1)" or "Reg(2)" data and the "Reg(3)" or "Reg(4)" data in parallel to the first and second devices 92 and 93. As a result, it is possible to shorten the communication time of the entire system.

Further, in the signal processing apparatus 94 according to the present embodiment, the communication standard of the CPU I/F 941 is PCIe. On the other hand, the communication standard of the first and second master-side communication units 943 and 944 is SPI. That is, the communication speed between the CPU 91 and the first to fourth virtual registers 942A to 942D is set to be relatively high.

Therefore, the CPU 91 may execute writing of the "Reg(1)" to "Reg(4)" data to the first to fourth virtual registers 942A to 942D which is the process of controlling the operations of the first to fourth processing modules 922, 923, 932, and 933, at high speed. That is, the CPU 91 may execute other processes after executing the process of controlling the operations of the first to fourth processing modules 922, 923, 932, and 933 at high speed. Therefore, it is possible to improve the processing efficiency of the CPU 91.

Further, since the SPI is adopted as the communication standard of the first and second master-side communication units 943 and 944, it is possible to suppress an increase in circuit scale and board area as compared with a case where the PCIe is adopted.

Other Embodiments

The embodiment for carrying out the disclosure has been described above, but the disclosure should not be limited only to the above-described embodiments.

In the above-described embodiment, the number of devices that communicate with the signal processing apparatus according to the disclosure is two (first and second devices 92 and 93), but the number of devices is not limited to two, and may be three or more. In addition, the number of processing modules provided in the device is two (first and second processing modules 922 and 923 or third and fourth processing modules 932 and 933), but the number of processing modules is not limited to two, and may be one or three or more. Further, some processing modules among all of the processing modules may be provided in the signal processing apparatus according to the disclosure. Further, the controller according to the disclosure may be provided in the signal processing apparatus according to the disclosure.

In the above-described embodiment, the signal processing apparatus according to the disclosure is configured by the FPGA, but is not limited thereto and may be configured by another programmable logic device, or application specific integrated circuit (ASIC). The same applies to the processing module according to the disclosure.

In the above-described embodiment, the communication standards of the first to third interfaces IF1 to IF3 and the buses Bu1 to Bu4 are not limited to the communication standards described in the above-described embodiments, and other communication standards may be adopted. For example, the communication standards of the second and third interfaces IF2 and IF3 may be the same PCIe as that of the first interface IF1.

In the above-described embodiment, a memory that temporarily stores the data (each data of "Reg(1)" to "Reg(4)" data) may be provided in the first and second slave-side communication units 921 and 931 as with the first and second master-side communication units 943 and 944.

In the above-described embodiment, two communication units (first and second master-side communication units 943 and 944) according to the disclosure are provided, but the number of communication units may be one or three or more.

In the above-described embodiment, the signal processing apparatus according to the disclosure is mounted on the medical observation system 1 in which the insertion portion 2 is configured by a rigid endoscope, but the disclosure is not limited thereto. For example, the signal processing apparatus according to the disclosure may be mounted on a medical observation system in which the insertion portion 2 is configured by a flexible endoscope. Further, the signal processing apparatus according to the disclosure may be mounted on a medical observation system such as a surgical microscope (for example, refer to Japanese Laid-open Patent Publication No. 2016-42981) which performs observation by enlarging a predetermined visual field region inside a subject (in a living body) or on the surface of a subject (surface of a living body). Furthermore, the signal processing apparatus according to the disclosure may be mounted on equipment used in fields other than the medical field.

In the above-described embodiment, a part of the configuration of the control device 9 may be provided in the connector CN1 or the connector CN2.

According to the signal processing apparatus of the disclosure, it is possible to improve convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A signal processing apparatus for relaying communication of control signals between a controller and a plurality of processing circuits, the signal processing apparatus comprising:
a communication circuit configured to receive the control signals from the controller, external to the signal processing apparatus, and send the control signals to the plurality of processing circuits in corresponding medical devices, external to the signal processing apparatus, wherein each medical device executes a specific process and includes one or more processing circuits;
a plurality of first storages provided respectively to correspond to the plurality of processing circuits, the plurality of first storages being configured to store the control signals written by the controller for a corresponding processing circuits of the plurality of processing circuits;
a second storage configured to store: address information indicating each communication address assigned to each of the plurality of processing circuits; and correspondence information indicating correspondence relationships between the plurality of first storages and a plurality of module-side storages respectively included in the plurality of processing circuits; and
a synchronization circuit configured to, in response from activation from a module of the plurality of processing circuits, synchronize the plurality of first storages with the plurality of corresponding module-side storages via the communication circuit based on the address information and the correspondence information and to output the control signals stored in a corresponding one of the plurality of first storages to the communication circuit to be sent to the module of the plurality of processing circuits.

2. The signal processing apparatus according to claim 1, wherein the communication circuit is provided in plurality.

3. The signal processing apparatus according to claim 1, wherein the communication circuit includes a third storage configured stores the control signals temporarily.

4. The signal processing apparatus according to claim 1, wherein
communication speed between the controller and the plurality of first storages is set to be faster than communication speed between the communication circuit and the plurality of processing circuits.

5. A control apparatus for controlling a camera head and a display, the control apparatus comprising:
a controller;
a plurality of processing circuits in corresponding medical devices, wherein each medical device executes a specific process and includes one or more processing circuits; and
a signal processing circuit including
a communication circuit configured to receive the control signals from the controller and send the control signals to the plurality of processing circuits,
a plurality of first storages provided respectively to correspond to the plurality of processing circuits, the plurality of first storages being configured to store the control signals written by the controller for a corresponding processing circuits of the plurality processing circuits,
a second storage configured to store: address information indicating each communication address assigned to each of the plurality of processing circuits; and correspondence information indicating correspondence relationships between the plurality of first storages and a plurality of module-side storages respectively included in the plurality of processing circuits, and
a synchronization circuit configured to, in response from activation from a module of the plurality of processing circuits, synchronize the plurality of first storages with the plurality of corresponding module-side storages via the communication circuit based on the address information and the correspondence information and to output the control signals stored in a corresponding one of the plurality of first storages to the communication circuit to be sent to the module of the plurality of processing circuits.

6. The control apparatus according to claim 5, wherein the communication circuit is provided in plurality.

7. The control apparatus according to claim 5, wherein the communication circuit includes a third storage configured stores the control signals temporarily.

8. The control apparatus according to claim 5, wherein communication speed between the controller and the plurality of first storages is set to be faster than communication speed between the communication circuit and the plurality of processing circuits.

9. The control apparatus according to claim 5, wherein each of the plurality of processing circuits includes a corresponding register.

10. A non-transitory computer readable storage having computer readable instructions that when executed by circuitry, cause the circuitry to relaying communication of control signals between a controller and a plurality of processing circuits in corresponding medical devices, wherein each medical device executes a specific process and includes one or more processing circuits, the circuitry configured to:
receive the control signals from the controller;
store the control signals in a plurality of first storages for corresponding processing circuit of the plurality of processing circuits;
store address information indicating each communication address assigned to each of the plurality of processing circuits and correspondence information indicating correspondence relationships between the plurality of first storages and a plurality of module-side storages respectively included in the plurality of processing circuits; and
in response from activation from a module of the plurality of processing circuits, synchronize the plurality of first storages with the plurality of corresponding module-side storages based on the address information and the correspondence information and output the control signals stored in a corresponding one of the plurality of first storages to the module of the plurality of processing circuits.

* * * * *